(12) United States Patent
Spellberg et al.

(10) Patent No.: US 11,701,346 B2
(45) Date of Patent: Jul. 18, 2023

(54) RIFABUTIN FOR THE TREATMENT OF ACINETOBACTER BAUMANNII

(71) Applicant: University of Southern California, Los Angeles, CA (US)

(72) Inventors: Brad Spellberg, Los Angeles, CA (US); Brian Luna, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 251 days.

(21) Appl. No.: 16/821,861

(22) Filed: Mar. 17, 2020

(65) Prior Publication Data

US 2020/0222373 A1 Jul. 16, 2020

Related U.S. Application Data

(63) Continuation of application No. 16/697,853, filed on Nov. 27, 2019, now abandoned.

(60) Provisional application No. 62/772,367, filed on Nov. 28, 2018.

(51) Int. Cl.
*A61K 31/438* (2006.01)
*A61P 31/04* (2006.01)

(52) U.S. Cl.
CPC ............ *A61K 31/438* (2013.01); *A61P 31/04* (2018.01)

(58) Field of Classification Search
CPC ........ A61K 31/438; A61K 38/12; A61P 31/04
See application file for complete search history.

(56) References Cited

PUBLICATIONS

Chromy et al., Future Microbiology, vol. 7, No. 8, (2012) [SciFinder Abstract provided].*
Luna et al., A Nutrient-limited Screen Unmasks Rifabutin Hyperactivity for XDR Acinetobacter baumanii, Nat Microbiol, 2020, vol. 5(9), pp. 1134-1143.
Blanchard et al., Identification of Acinetobacter baumannii serum-associated antibiotic efflux pump inhibitors, Antimicrob Agents Chemother, 2014, vol. 58(11), pp. 6360-6370.
Bruhn et al., Host fate is rapidly determined by innate effector-microbial interactions during Acinetobacter baumannii bacteremia, J Infect Dis , 2015, vol. 211(8), pp. 1296-1305.
Durante-Mangoni et al., Colistin and rifampicin compared with colistin alone for the treatment of serious infections due to extensively drug-resistant Acinetobacter baumannii: a multicenter, randomized clinical trial, Clin Infect Dis., 2013, vol. 57(3), pp. 349-358.
Lin et al., Inhibition of LpxC protects mice from resistant Acinetobacter baumannii by modulating inflammation and enhancing phagocytosis, MBio., 2012, vol. 3(5):p. e00312-12.
Luo et al., Active and passive immunization protects against lethal, extreme drug resistant-Acinetobacter baumannii Infection, PLoS One, 2012, vol. 7(1), p. e29446.
Maragakis et al., baumannii: epidemiology, antimicrobial resistance, and treatment options, Clin Infect Dis 2008, vol. 46(8), pp. 1254-1263.
Nielsen et al., Monoclonal Antibody Protects Against Acinetobacter baumannii Infection by Enhancing Bacterial Clearance and Evading Sepsis, J Infect Dis., 2017, vol. 216(4), pp. 489-501.
Sun et al., Rapid antimicrobial susceptibility test for identification of new therapeutics and drug combinations against multidrug-resistant bacteria, Emerg Microbes Infect 2016, vol. 5(11), pp. e116.
Yoon et al., In vitro double and triple synergistic activities of Polymyxin B, imipenem, and rifampin against multidrug-resistant Acinetobacter baumannii, Antimicrob Agents Chemother 2004, vol. 48(3), pp. 753-757.
Phillips et al., Pharmacology, Dosing and Side Effects of Rifabutin as a Possible Therapy for Antibiotic-Resistant Acinetobacter Infections, Open Forum Infectious Diseases, 2020, vol. 7(11), pp. 1-9.
Cheng et al., Synergistic Rifabutin and Colistin Reduce Emergence of Resistance When Treating Acinetobacter baumannii, Antimicrobial Agents Chemotherapy, 2021, vol. 65(4).
Lee et al., In Vitro Activity of Rifabutin and Rifampin against Antibiotic-Resistant Acinetobacter baumannii, *Escherichia coli, Staphylococcus aureus*, Pseudomonas aeruginosa, and Klebsiella pneumoniae, mSphere, 2021, vol. 6(6), pp. 1-9.
Chromy et al., Repurposing screen identify rifamycins as potential broad-spectrum therapy for multidrug-resistant Acinetobacter baumannii and select agent microorganisms, Future Microbiology, 2012, vol. 7(8).
U.S. National Library of Medicine, Colistin and Rifampicin for MDR-Acinetobacter (CoRAb), NCT01577862, ClinicalTrials.gov, retrieved from the internet: https://clinicaltrials.gov/ct2/show/NCT01577862.

* cited by examiner

*Primary Examiner* — Alicia L Otton
(74) *Attorney, Agent, or Firm* — Nixon Peabody LLP; Linda B. Huber; Suwei Zhu

(57) ABSTRACT

To identify novel agents to treat carbapenem-resistant *Acinetobacter baumannii*. the Inventors used a nutrient-depleted medium with serum to mimic the in vivo environment. In RPMI with serum, the screen identified rifabutin (RBT) as being 133-fold more potent than rifampin (RIF) against *A. baumannii*, with MICs of 0.031 µg/ml and 4 µg/ml respectively. No difference in RBT vs. RIF activity was observed when MHII was used as the culture media. RBT possesses markedly superior in efficacy to RIF in murine models of lethal iv and pneumonia models of infection with a hyper-virulent, clinical lung and blood isolate of extreme-drug resistant (XDR) *A. baumannii*. In both models, RBT significantly improved survival and lowered bacterial burden compared to RIF. RBT is a promising, novel therapeutic option for *A. baumannii* infections.

18 Claims, 10 Drawing Sheets

RIFABUTIN FOR THE TREATMENT OF ACINETOBACTER BAUMANNII

CROSS REFERENCE TO OTHER APPLICATIONS

This application is a continuation U.S. Nonprovisional application Ser. No. 16/697,853, filed Nov. 27, 2019, which is pending, and claims the benefit of U.S. Provisional Application No. 62/772,367, filed Nov. 28, 2018.

STATEMENT REGARDING FEDERALLY SPONSORED RESEARCH OR DEVELOPMENT

This invention was made with government support under Grant No. AI117211 awarded by National Institutes of Health. The government has certain rights in the invention.

FIELD OF THE INVENTION

Described herein are methods and compositions related to antibiotics and antibiotic resistance. The described method and compositions related to identifying, delivering and designing effective therapeutics for combating antibiotic resistance.

BACKGROUND

Antimicrobial resistance is a tremendous global concern. Antibiotic-resistant Gram-negative bacteria have spread widely through global health care systems. Increasingly they have become resistant to all antibiotics available for treatment, i.e. pan-drug resistant (PDR). Examples of these PDR Gram-negative bacteria include *Acinetobacter baumannii* (Spellberg et al., Combating antimicrobial resistance: policy recommendations to save lives, Clin Infect Dis. 2011, 52 Suppl 5:S397-428; Wong et al, Clinical and Pathophysiological Overview of *Acinetobacter* infections: A century of challenges, Clin Microbiol Rev 2017, 30:409-47).

*Acinetobacter baumannii* (*A. baumannii*), a ubiquitous pathogen capable of causing both community and health care-associated infections (HAIs), has emerged recently as a major cause of HAI due to the extent of its antimicrobial resistance and its propensity to cause large, often multi-facility, nosocomial outbreaks (Fournier et al., The epidemiology and control of *A. baumannii* in health care facilities, Clin Infect Dis. 2006, 42(5):692-9, Epub). *Acinetobacter* species accounted for 1.5% of all nosocomial bloodstream infections (BSIs) reported and is increasingly frequently associated with nosocomial pneumonia in intensive care units (ICUs), the incidence of which has increased from 4% in 1986 to 7% in 2003. In addition, *A. baumannii* is associated with bacteremia, urinary tract infections and surgical-site infections (Gaynes et al., Overview of nosocomial infections caused by gram-negative bacilli, Clin Infect Dis. 2005, 41(6):848-54, Epub; Wong et al., Clinical and Pathophysiological Overview of *Acinetobacter* infections: A century of challenges, Clin Microbiol Rev 2017, 30:409-47).

*Acinetobacter* is one of several Gram-negative species that routinely demonstrates an XDR phenotype, the hallmark of which is carbapenem resistance. XDR is defined as resistance to all available systemic antibiotics except for those that are known to be less effective or more toxic compared to first-line agents that are used to treat susceptible pathogens (Infectious Diseases Society of America. White Paper: Recommendations on the Conduct of Superiority and Organism-Specific Clinical Trials of Antibacterial Agents for the Treatment of Infections Caused by Drug-Resistant Bacterial Pathogens. 2012. Clin Infect Dis. 55:1031-46). Thus, infections caused by XDR *A. baumannii* are generally only treatable with often toxic, not always very effective second-line agents, such as tigecycline or polymyxins. Such infections cause longer hospitalization, increased costs, and greater mortality than infections caused by carbapenem-susceptible strains. Indeed, due to their resistance to first-line agents, XDR *A. baumannii* bloodstream infections result in 50 to 60% mortality (Wong et al., 2017, op.cit.).

But pulmonary patients infected by multiresistant *A. baumannii* treated with the non-traditional agent polymyxin B or colistin have not responded well to such monotherapy, and resistance has occurred among strains that have persisted during treatment. For this reason therapy with multiple antibacterial agents is often used by practitioners (Maragakis L L and Perl T M, *Acinetobacter baumannii*: epidemiology, antimicrobial resistance, and treatment options. Clin Infect Dis 2008, 46(8): 1254-63). This high unmet medical need has brought recent research to focus on the search of synergistic double and triple combination of multiple agents with or without antibacterial activity against multidrug-resistant *A. baumannii* (Yoon et al., In vitro double and triple synergistic activities of Polymyxin B, imipenem, and rifampin against multidrug-resistant *Acinetobacter baumannii*, Antimicrob Agents Chemother 2004, 48(3):753-7) (Sun W, et al., Rapid antimicrobial susceptibility test for identification of new therapeutics and drug combinations against multidrug-resistant bacteria. Emerg Microbes Infect 2016, 5(11):e116).

Thus, there is a high need for new therapeutic agents to treat infections caused by drug resistant bacteria such as *Acinetobacter* bacteria, since such infections are a leading threat to public health.

SUMMARY OF THE INVENTION

Described herein are methods and compositions related to the treatment of *Acinetobacter* infections in humans with rifabutin. In one embodiment, the method of treatment includes administering rifabutin to a subject in need thereof. In various embodiments, the subject in need thereof is infected with *Acinetobacter*. In various embodiments, the rifabutin is administered as sole therapeutically active agent to treat said *Acinetobacter* infection. In various embodiments, the is not co-administered with any other therapeutically active agent that is being administered to treat the same *Acinetobacter* infection. In various embodiments, the *Acinetobacter* infection is *Acinetobacter baumannii*. In various embodiments, the rifabutin is administered to a human patient. In various embodiments, the method includes a time lag of at least about 48 h, preferably at least about 24 h, more preferably at least about 12 h, again more preferably about at least 8 h, again more preferably at least about 4 h is between administration of rifabutin and administration of another antibiotic that is administered to treat the same *Acinetobacter* infection. In various embodiments, the *Acinetobacter* infection is caused by multi-drug resistant *Acinetobacter* bacteria. In various embodiments, the *Acinetobacter* infection is selected from the group consisting of: respiratory tract, blood, circulation system, urinary tract, skin, surgical-site, and meningitis; preferably said infection is an infection of respiratory tract or blood. In various embodiments, the *Acinetobacter* infection is a nosocomial *Acinetobacter* infection. In various embodiments, the rifabutin is administered in a dose of 60 mg to 600 mg per day.

Further described herein are methods and compositions related to the addition of rifabutin therapy to other antibiotics as a combination regimen to treat *Acinetobacter* infections.

Also described herein are methods and compositions related to the method of using RPMI-based media as a screen for in vitro antimicrobial activity of compounds that is more predictive of in vivo efficacy than traditional rich media used to grow microbes.

Further described herein is a pharmaceutical composition including a quantity of rifabutin and a pharmaceutically acceptable carrier.

DETAILED DESCRIPTION OF THE INVENTION

Figure 1:
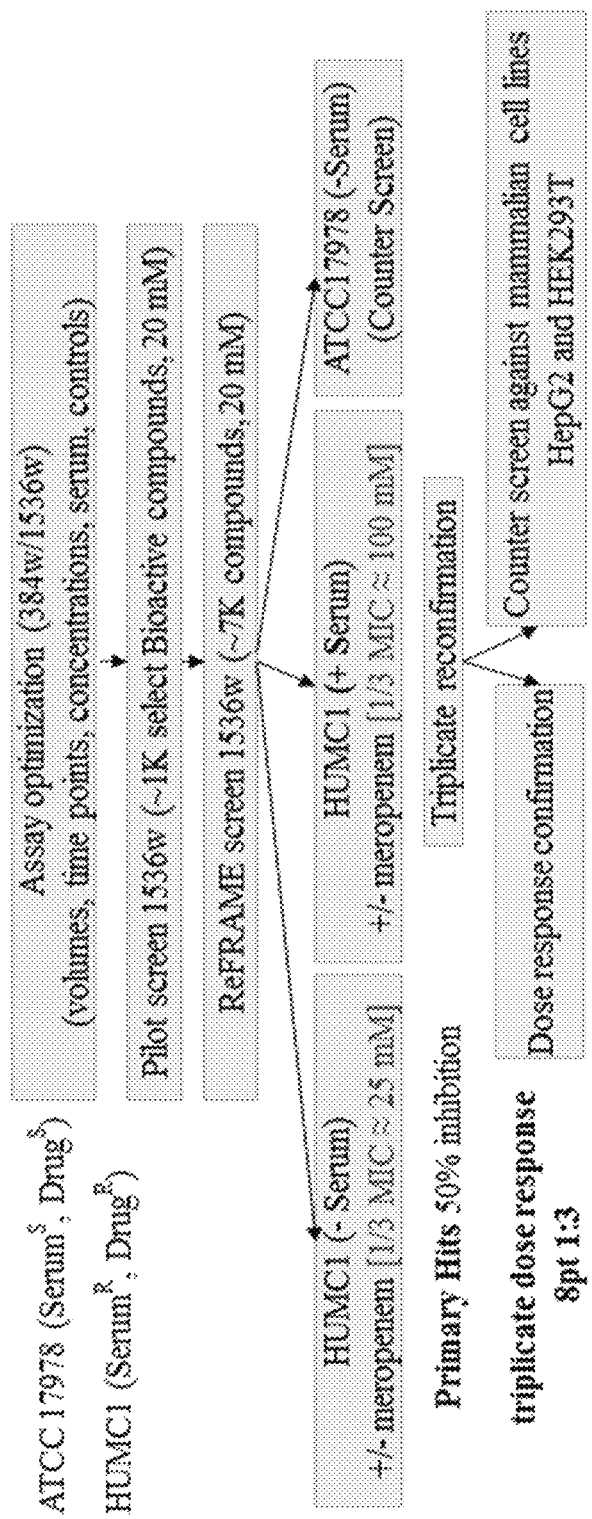
FIG. 1. Summary of the compound screening assay used for the identification of rifabutin. The ReFRAME compound library, a curated chemical library that is comprised of structurally and functionally diverse chemicals, including FDA approved drugs. 11,862 chemicals werE screened in total and rifabutin was identified as the most active hit.

Throughout this specification and the claims which follow, unless the context requires otherwise, the word "comprise", and variations such as "comprises" and "comprising", are to be understood to imply the inclusion of a stated integer or step or group of integers or steps but not the exclusion of any other integer or step or group of integer or step.

As used in this specification and the appended claims, the singular forms "a", "an", and "the" include plural referents, unless the content clearly dictates otherwise.

The term "about" when used in connection with a numerical value is meant to encompass numerical values within a range having a lower limit that is 0-10% smaller than the indicated numerical value and having an upper limit that is 0-10% larger than the indicated numerical value.

The term "therapeutically active agent" as used herein refers to any substance which is intended to furnish therapeutic activity, i.e. which is intended to furnish a direct effect in the cure, mitigation, treatment or prevention of a disease, disorder or condition.

The term "to administer", "administration" or "administered", as used interchangeably herein, means to introduce a therapeutically or pharmaceutically active agent into the body of a subject in need thereof to treat or prevent a disease, disorder or condition.

The term "treatment", "treating", or "therapy", as used interchangeably herein, refers to the management and care of a patient having a pathology, preferably an infection, for which administration of one or more therapeutic compounds is indicated for the purpose of combating or alleviating symptoms and complications of said pathology conditions. Treating includes administering rifabutin in order to prevent the onset of the symptoms or complications, alleviating the symptoms or complications, or eliminating the disease, condition, or disorder. As used herein, "treatment" refers to therapeutic treatment, and prophylactic or preventative measures.

The term "patient" is used herein to mean preferably a subject suffering from, being at risk of suffering from, or being potentially capable of suffering from a disease, disorder or condition. Said disease is preferably an infection, more preferably an *Acinetobacter* infection, again more preferably an *Acinetobacter baumannii* infection. The term "patient" is used herein to mean preferably an animal, more preferably a mammal (including a human). Most preferred, the patient is a human.

The term "therapeutically effective amount" as used herein refers to an amount of an agent, preferably rifabutin, which is effective to treat at least one symptom of an infection. Amounts of an agent for administration may vary based upon the desired activity, the diseased state of the patient being treated, the dosage form, method of administration, patient factors such as the patient's sex, weight and age, the underlying cause of the condition or disease to be treated, the route of administration and bioavailability, the persistence of the administered agent in the body, the formulation, and the potency of the agent.

Rifabutin is administered as the sole therapeutically active agent to treat said *Acinetobacter* infection in the absence of co-administration of any other therapeutically active agent that is being administered to treat the same *Acinetobacter* infection, to which it is referred herein as "single active agent therapy" or administration as "single active agent".

Said other therapeutically active agent is preferably an antimicrobial, more preferably an antibiotic. The term "antimicrobial" as used herein refers to an agent that kills any type of microorganisms (i.e. incl. microbicidal) or stops or inhibits growth of microorganisms (i.e. incl. biostatic) and includes and are preferably antibacterials (antibiotics), antifungals, antivirals, antiprotozoics and antiparasitics. In a more preferred embodiment, said antimicrobial is an antibiotic. The term "antibiotic" as used herein refers to an agent that kills bacteria or stops or inhibits growth of bacteria. In an again more preferred embodiment, said antibiotic is selected from the group consisting of colistin, imipenem, polymyxins (including polymyxin B and E), trimethoprim, aztreonam, ceftazidime, trimethoprim, and aztreonam.

The term "infection" or "infectious disease", as used interchangeably herein, refers to the invasion of body tissues by infectious pathogens, their multiplication, and the reaction of body tissues to the infectious pathogens and the toxins they produce. The term "infection" includes and refers preferably to chronic infections (long-term), acute infections (short-term), symptomatic infections (apparent, clinical), subclinical infections (inapparent, silent or occult), latent infection (inactive or dormant), systemic infection, local infection, primary infections, secondary infections and opportunistic infections.

The terms "*Acinetobacter* infection" and "infection caused by *Acinetobacter*", as used interchangeably herein, refers preferably to an infection, wherein bacteria of the genus *Acinetobacter* cause, at least in part, or participate in induction, development or course of said *Acinetobacter* infection. An *Acinetobacter* infection is most preferably an infection wherein bacteria of the genus *Acinetobacter* can be detected in samples of the affected tissue or cells.

The invention presents herein a new approach for the treatment of highly lethal, antibiotic-resistant infections caused by bacteria of the genus *Acinetobacter*, preferably *A. baumannii*.

Rifabutin is a well-known and safe antibiotic currently used in the clinical practice for the treatment of *Mycobacterium avium* complex (MAC) and tuberculosis infections in AIDS patients (cf. Mycobutin (Rifabutin), USP description at https://www.accessdata.fda.gov). Clinical use of rifabutin for the treatment of infections caused by *A. baumannii* has never been considered due to the poor in vitro activity of rifabutin tested under CLSI (Clinical & Laboratory Standards Institute) and EUCAST (European Committee on Antimicrobial Susceptibility Testing) conditions which recommends testing of *A. baumannii* in Mueller-Hinton-based media. When tested under this conditions, MICs of rifabutin and of other members of this antibiotic class, e.g., rifampin, against *Acinetobacter baumannii* are too high and these drug levels are considered unachievable in humans for an effective treatment of the infection and/or eradication of the pathogen. Based on these evidences, two recent papers sought synergistic activities among drugs so that MIC of rifampin (Yoon J, et al., In vitro double and triple synergistic activities of polymyxin B, imipenem, and rifampin against multidrug-resistant *Acinetobacter baumannii*. Antimicrob Agents Chemother 2004, 48(3):753-7) or of rifabutin (Sun W, et al., Rapid antimicrobial susceptibility test for identification of new therapeutics and drug combinations against multidrug-resistant bacteria. Emerg Microbes Infect 2016, 5(11):e116) could be lowered to levels potentially achievable in humans. Caveat of both publication is that the observed in vitro synergy was not verified in any animal infection model; indeed, it is well known that for synergy among drugs to occur in vivo, all drugs must be present at the same time and at the correct concentrations at the infection site and this is dependent from the pharmacokinetics, which include the distribution into tissues, of each single drug. This is a well-known limit to the approach.

Contrary to the above approach, the inventors had the novel ideal to test a series of antibiotics in RPMI, a medium that, although commonly used in cell and tissue culture for growing a variety of eukaryotic cell, is not routinely used for bacterial cultures. The rationale for testing RPMI is that standard methodologies for determining antibiotic susceptibilities use rich culture media, which may not reflect the hostile in vivo environment with respect to supporting microbial growth. Since RPMI is used as a culture media for human and mammalian cells, the idea was determine if cryptic, hidden, or previously undetectable antimicrobial activity could be unmasked when many drugs were screened for such activity in RPMI media, rather than traditional rich culture media.

In a drug screen of more than 8,000 compounds, surprisingly, the inventors discovered that MICs of rifabutin against *Acinetobacter baumannii* were up to 200-fold lower in RPMI than in a Mueller-Hinton-based medium such as CAMHB (cation-adjusted Mueller-Hinton broth). Even more surprisingly, only the MIC of rifabutin dropped from 3.125 µg/ml down to 0.0156 µg/ml against *A. baumannii* HUMC1 (a hyper-virulent, clinical bloodstream isolate), but not that of the closely related rifampin which showed an MIC of 3.125 µg/ml in both RPMI and CAMHB. Similarly the MICs of other rifamycins were not shifted in RPMI vs. CAMHB media; only rifabutin's MICs shifted.

This discovery revealed for the first time that the MIC of rifabutin are significantly lower than previously reported when tested in mammalian culture media rather than rich media and, consequently, rifabutin drug levels are fully achievable in humans for an effective treatment of the infection and eradication of *Acinetobacter baumannii*.

To prove that the MIC shift seen for rifabutin in RPMI medium was indeed predictive of a good in vivo efficacy against *Acinetobacter baumannii* infections, rifabutin was tested for the first time ever in several animal infection models using rifampin as comparator.

Rifabutin was first tested in a well-validated *Acinetobacter baumannii* infection model generated in *Galleria mellonella* in a dose-response manner against rifampin. The data confirmed that MIC of rifabutin generated in RPMI medium were more predictive than those generated in CAMHB in predicting in vivo efficacy: whereas rifampin showed only a partial protection at doses as high as 5 mg/kg, rifabutin was efficacious at doses as low as 0.1 mg/kg.

Rifabutin's superior in vivo efficacy was confirmed in two different *A. baumannii* animal infection models, which are highly predictive of efficacy in humans: the murine bacteremia and the murine pneumonia. Similarly to the *A. baumannii* infection in the *Galleria mellonella* model, in the murine bacteremia infection model rifabutin was fully protective at 0.1 mg/kg whereas rifampin at 10 mg/kg gave only 50% protection. In the murine pneumonia infection model caused by *A. baumannii*, rifabutin and rifampin were compared at the same dose of 5 mg/kg and the treatment-related daily survival rates and reduction of bacterial burden at day 7 post-infection were recorded: Rifampin did not protect from mortality similarly to the vehicle control, but rifabutin improved survival rates by over 70%. Parallelly, bacterial counts of rifampin at day 7 were similar to those of the vehicle control ($Log_{10}$ (CFU/mg lung) of 6.5) whereas rifabutin reduced bacterial burden down to about 2 $Log_{10}$ (CFU/mg lung). Hence, rifabutin is much more potent than rifampin at killing *A. baumannii* not only in vitro but also in vitro, i.e. in treating *A. baumannii* infections. These results confirm the previously unknown in vivo activity of rifabutin against *A. baumannii*, and validate that the in vitro susceptibility testing of novel antimicrobial compounds in RPMI-based media can be more predictive of in vivo antimicrobial activity in mammals than traditional rich media testing.

Thus rifabutin, used as the sole therapeutically active agent to treat said *Acinetobacter* infection in the absence of co-administration of any other therapeutically active agent that is being administered for the only purpose of exercising synergy with rifabutin to treat the same *Acinetobacter* infection, provides an efficacious treatment of diseases caused by this pathogen as demonstrated in several animal models of infection.

*Acinetobacter baumannii* is one of the most drug resistant bacterial pathogens. Blood or lung infections caused by extreme drug resistant (XDR) *A. baumannii* cause 50% mortality rates, and the antimicrobial pipeline for such infections is inadequate. Discovery of new antibiotics has traditionally occurred via high throughput screening assays. These assays use rich media, such as Mueller-Hinton II (MHII) broth and rarely identify any new candidates now. However, modifying the screen by changing the media to be more reflective of the in vivo environment has enabled discovery of novel compounds.

There is a critical need to develop new therapeutics to treat carbapenem-resistant *A. baumannii* infections. In this study the Inventors conducted a high throughput, modified chemical screening approach which led to the "unmasking" of rifabutin activity in vitro when the bacteria were cultured in RPMI, but not in MHII media.

To increase the probability of identifying novel agents that would be effective in vivo, we screened for activity in a nutrient-depleted medium with serum to mimic the host environment. We screened a library of 11,862 compounds against *A. baumannii* cultured in RPMI with serum, or in traditional, nutrient-rich Mueller-Hinton (MHII) media. In RPMI with serum, the screen identified rifabutin (RBT) as being 133-fold more potent than rifampin (RIF) against *A. baumannii*, with MICs of 0.031 µg/ml and 4 µg/ml respectively. However, no difference in RBT vs. RIF activity was observed when MHII was used as the culture media (MIC=4 µg/ml for both). The activity in the depleted media better predicted in vivo efficacy since RBT was markedly superior in efficacy to RIF in lethal models of extreme drug resistant (XDR) *A. baumannii* bacteremia and pneumonia in mice, and in a lethal *Galleria* model of infection. In all models, RBT markedly improved survival and lowered bacterial burden compared to RIF. The mechanism of enhanced efficacy of RBT vs. RIF was a Trojan horse-like, selective, import of RBT but not RIF intracellularly in *A. baumannii*. Free aromatic amino acids, specifically histidine and tryptophan, were the constituents of rich media that antagonized the potency of RBT such that it became similar to RIF, and acted by antagonizing the Trojan horse-like uptake of RBT by the bacteria. Furthermore, administering free amino acids to the bloodstream of mice during infection also antagonized RBTs enhanced activity. Thus we identify RBT as a promising, novel therapeutic option for *A. baumannii* infections. RBT, but not RIF, is selectively imported into *A. baumannii* in a manner antagonized by free aromatic amino acids. As such, screening in traditional media was not capable of detecting the phenomenon, while screening in nutrient depleted media plus serum much better predicted in vivo efficacy in multiple animal models. Given that RBT is already commercially available, these results can be immediately translated to clinical trials.

These results that free amino acids in the MHII inhibit the activity of rifabutin. Lastly, the Inventors further demonstrate the superiority of rifabutin over rifampin in mouse models of bacteremia and oral aspiration pneumonia disease models.

Described herein is the use of Rifabutin in the treatment of an *Acinetobacter* infection. In a first aspect, the invention relates to rifabutin for use in the treatment of an *Acinetobacter* infection, wherein Rifabutin is administered as the sole therapeutically active agent to treat said *Acinetobacter* infection in the absence of co-administration of any other therapeutically active agent that is being administered to treat the same *Acinetobacter* infection.

In a preferred embodiment, the invention refers to a method for treating an *Acinetobacter* infection, wherein a therapeutically effective amount of Rifabutin is administered as the sole therapeutically active agent to treat said *Acinetobacter* infection in the absence of co-administration of any other therapeutically active agent that is being administered to treat the same *Acinetobacter* infection to a patient.

In various embodiments, administration is to a subject that is a mammalian, more preferably a human patient. In a preferred embodiment, in the method for treating said *Acinetobacter* infection, a therapeutically effective amount of Rifabutin is administered to a mammalian, more preferably a human patient. In various embodiments, Rifabutin is administered as the sole therapeutically active agent to treat said *Acinetobacter* infection in the absence of co-administration of any other therapeutically active agent that is being administered to treat the same *Acinetobacter* infection, to which it is referred herein as "single active agent therapy" or administration as "single active agent".

In a preferred embodiment, said *Acinetobacter* infection is an infection caused by bacteria selected from the group consisting of *Acinetobacter baumannii, Acinetobacter lwoffii, Acinetobacter calcoaceticus, Acinetobacter nosocomialis, Acinetobacter pittii, Acinetobacter haemolyticus, Acinetobacter johnsonii, Acinetobacter junii, Acinetobacter schindleri, Acinetobacter ursingii,* and *Acinetobacter seifertii*. In another preferred embodiment, said *Acinetobacter* infection is an infection caused by bacteria selected from the group consisting of *Acinetobacter baumannii, Acinetobacter lwoffii, Acinetobacter calcoaceticus, Acinetobacter nosocomialis,* and *Acinetobacter pittii*. Most preferably, said *Acinetobacter* infection is an infection caused by *Acinetobacter baumannii*.

In a preferred embodiment of the invention, Rifabutin is used in the treatment of an *Acinetobacter baumannii* infection in a human patient.

In another preferred embodiment, said *Acinetobacter* infection is caused by a multi-drug resistant (MDR) *Acinetobacter* bacteria. The term "multi-drug resistant bacteria" preferably refers to bacteria with an in vitro resistance to more than one antimicrobial. More preferably, MDR bacteria are defined as acquired non-susceptibility to at least one antimicrobial in three or more antimicrobial categories (cf. Magiorakos et al., Multidrug-resistant, extensively drug-resistant and pandrug-resistant bacteria: an international expert proposal for interim standard definitions for acquired resistance, Clin Microbiol Infect 2012; 18: 268-281). Antimicrobial categories and agents used to define MDR, XDR and PDR can be also found in Magiorakos et al., 2012 (op.cit.)

In another preferred embodiment, said multi-drug resistant *Acinetobacter* bacteria are extremely drug resistant *Acinetobacter* bacteria (i.e. extensively drug resistant, XDR bacteria) or pandrug-resistant *Acinetobacter* bacteria (PDR bacteria). In another preferred embodiment, said multi-drug resistant *Acinetobacter* bacteria are XDR bacteria. In another preferred embodiment, said multi-drug resistant *Acinetobacter* bacteria are PDR bacteria. XDR is preferably defined as non-susceptibility to at least one agent in all but two or fewer antimicrobial categories (i.e. bacterial isolates remain susceptible to only one or two categories), and PDR is preferably defined as non-susceptibility to all agents in all antimicrobial categories (Magiorakos et al., 2012, op.cit.)

In another preferred embodiment, said *Acinetobacter* infection is selected from the group consisting of an *Acinetobacter* infection of the respiratory tract, blood (i.e. bacteremia), circulation system, urinary tract, skin, surgical-site, catheter-site and meningitis. In another preferred embodiment, said *Acinetobacter* infection is selected from the group consisting of an *Acinetobacter* infection of the respiratory tract, blood, urinary tract, skin, and meningitis. In another more preferred embodiment, said *Acinetobacter* infection is an infection of respiratory tract or blood. In another more preferred embodiment, said *Acinetobacter* infection is an infection of the lung (pneumonia) or blood.

In another preferred embodiment, said *Acinetobacter* infection is a nosocomial infection. The term "nosocomial infection" as used herein refers to an infection that is acquired in a hospital or other health care facility (e.g., nursing home, rehabilitation facility, outpatient clinic, or other clinical settings) and includes healthcare associated infections and hospital acquired infections.

In another preferred embodiment, rifabutin is administered in a daily dose of 60 mg to 600 mg as sole therapeutically active agent to treat said *Acinetobacter* infection in the absence of co-administration of any other therapeutically active agent that is being administered to treat the same *Acinetobacter* infection. In another preferred embodiment, rifabutin is administered as single active agent in a daily dose of 60 mg to 600 mg in 1-3 doses per day.

In a further aspect, the invention relates to a pharmaceutical composition comprising rifabutin as sole active agent for use in the treatment and/or prevention according to the invention.

In a further aspect, the invention relates to rifabutin for use in the treatment of an *Acinetobacter* infection, wherein rifabutin is administered in a daily dose of 60 mg to 600 mg. Rifabutin can be administered in a daily dose of 60 mg to 600 mg either as single active therapy or in combination with another therapeutically active agent that is co-administered to treat the same *Acinetobacter* infection. In a preferred embodiment, the invention refers to a method for treating an *Acinetobacter* infection, wherein rifabutin is administered in a daily dose of 60 mg to 600 mg to a patient.

In a preferred embodiment, said daily dose of 60 mg to 600 mg of rifabutin is used in the treatment of an *Acinetobacter* infection in a mammalian, more preferably a human patient.

In another preferred embodiment, said *Acinetobacter* infection is an infection caused by bacteria selected from the group consisting of *Acinetobacter baumannii, Acinetobacter lwoffii, Acinetobacter calcoaceticus, Acinetobacter nosocomialis,* and *Acinetobacter pittii*. In the most preferred embodiment, said *Acinetobacter* infection is an *A. baumannii* infection.

In a preferred embodiment, said daily dose of 60 mg to 600 mg of rifabutin is used in the treatment of an *Acinetobacter baumannii* infection in a human patient.

In another preferred embodiment, said *Acinetobacter* infection is caused by multi-drug resistant *Acinetobacter* bacteria, preferably XDR bacteria or PDR bacteria.

In another preferred embodiment, said *Acinetobacter* infection is selected from the group consisting of an *Acinetobacter* infection of the respiratory tract, blood (i.e. bacteremia), circulation system, urinary tract, skin, surgical-site, catheter-site and meningitis. In another preferred embodiment, said *Acinetobacter* infection is selected from the group consisting of an *Acinetobacter* infection of the respiratory tract, blood, urinary tract, skin, and meningitis. In another more preferred embodiment, said *Acinetobacter* infection is an infection of respiratory tract or blood. In another more preferred embodiment, said *Acinetobacter* infection is a nosocomial *Acinetobacter* infection.

The invention will now be illustrated by the following non-limiting Examples.

Example 1

Materials and Methods

Bacteria Culture
Frozen Stock:

Working solutions of bacteria were prepared using frozen stocks of *Acinetobacter baumannii, Klebsiella pneumonia,* and *Staphylococcus aureus* strains used for MIC testing, which were prepared as previously published.[14] The bacterial frozen stocks were diluted to ~1×10$^6$ CFU/mL for plating using Mueller Hinton II (MHII) broth or RPMI 1640 (Gibco #11875-085).

Fresh Culture:

Overnight cultures of *A. baumannii* and *Escherichia coli* were grown in Tryptic Soy Broth (TSB) at 37° C. The overnight culture was diluted 1:100 and then subcultured in MHII at 37° C./200 rpm until the culture reached an OD$_{600}$ of 0.5. The bacterial density was adjusted to 1×10$^6$ CFU/mL by dilution in the same medium used for the MIC, either MHII or RPMI.

Antibiotic Preparation:

A fresh stock of RBT and RIF was prepared each week for the MIC assay. For in vitro testing, the stock solution was prepared by dissolving RBT or RIF in 100% DMSO. The working solution of antibiotic was prepared 2× of the desired starting well final drug concentration. The antibiotic working solution dilutions were prepared in the respective media used for the MIC, MHII or RPMI.

MIC Protocol: The medium used for the minimum inhibitory concentration (MIC) assays performed in this study was either MHII or RPMI 1640. All of the MICs were performed in sterile 96-well round bottom microwell plates.

Briefly, 100 μl of media, RPMI or MHII, was added to the wells in columns 2-10. Column 11 served as a positive control for each of the conditions. One hundred μl of the respective media was added to the wells in this column while 200 μl of the media was added to column 12, which served as the negative control. Next, 200 μl of a 2× rifabutin or rifampin working solution was added to the wells in column 1. Two-fold serial dilutions of the antibiotic were performed through column 10. Next, 100 μl of a 1×10$^6$ CFU/mL working solution of bacteria was added to each of the wells in columns 1-11. The inoculum concentration was confirmed by plating serial dilutions on TSA plates.

To test the effect of the individual components of MHII, MHII fractions (size separation, acetonitrile extracted, proteinase K digested, or sodium periodate oxidized), 10 μL of the purified fraction was added to the appropriate wells. Amino acids (essential, non-essential, or individual amino acids) were added to the MIC at final concentrations summarized in Table 6. The individual components were also added to the positive and negative controls to confirm that there are no adverse effects as a result of the addition of these solutions. The MIC plates were incubated for 24 hours at 37° C.

Fractionation of MHII:

10×MHII was used for the fractionation to maximize the concentration of the MHII components. The media was filtered through a 0.22 μM filter and then the media was run through 10 and 30 kDa molecular weight cut-off (MWCO) centrifugal filtration columns at 12,000 g for 20 minutes. The >30 kDa fraction was collected and reserved for experimentation. The flow through was collected and transferred to a 10 kDa MWCO column. The centrifugation step was repeated as previously stated. The <10 kDa flow through was collected from this column. The 10<X<30 kDa fraction was collected as well.

Acetonitrile Extraction:

The organic and inorganic layers were separated with a liquid-liquid extraction by mixing the purified MHII fraction 1:1 with 100% acetonitrile. The sample was vortexed thoroughly and centrifuged at maximum speed for 10 minutes. The aqueous and organic layers were transferred to clean microcentrifuge tubes. To ensure the removal of any residual acetonitrile, the extracted MHII sample was dried using a SpeedVac and then resuspended in the original volume using sterile molecular grade H2O.

Proteinase K Digestion:

30 μl of proteinase K (Invitrogen, #46-7603) was added to 1 mL of the MHII<10 kDa fraction (organic extract or non-extracted as a control). The media was incubated at 65° C. for 1 hour. To inactivate the proteinase K, the sample was then incubated at 80° C. for 15 minutes.

Sodium Periodate Oxidation (Source #1):

Sodium periodate oxidation was done as previously described. Briefly, to oxidize the carbohydrates in the organic layer of the medium, sodium periodate (NaIO4) was added to the <10 fraction at a final concentration of 10 mM. The sample was incubated at room temperature for 30 minutes. Following incubation, the sodium periodate was quenched using 0.1 mL of 50% glycerol for every 1 mL of reaction. The sample was incubated at room temperature for 1 hour before downstream application.

Amino Acid Additions:

As indicated, amino acids were used to supplement the media for MIC testing. Mixed amino acids were tested by adding 10 μL of Gibco® MEM Amino Acids Solution (Thermo Scientific, #11130051) and Gibco® MEM Non-Essential Amino Acids (Thermo Scientific, #11140050) to each well in the MIC assay. Additionally, the effect of individual amino acids on the MIC was tested by the addition of purified amino acids at the same concentration contained in the Gibco mixed amino acid solutions listed above. Amino acids were prepared fresh and filter sterilized solutions prior to use.

Mouse Studies
Intravenous (IV) Infection:

*A. baumannii* HUMC1 frozen stock was prepared as described in previous work. Frozen stocks of HUMC1 were thawed and diluted in PBS to adjust the bacterial density as needed for infection. C3HeB/FeJ mice, 8 to 14 weeks old, were infected with 2×10$^7$ CFUs via tail vein injection and the inoculum bacterial density was confirmed by plating serial dilutions on TSA plates and incubating overnight at 37° C.

Oral Aspiration (OA) Infection:

Single colonies of *A. baumannii* HUMC1 grown on TSA were used to inoculated TSB and bacteria were cultured overnight at 37° C./200 rpm. The following day, the bacteria was subcultured by diluting the overnight 1:100 in fresh TSB and cultured for 3 hrs at 37° C./200 rpm. The subculture was washed with PBS three times and adjust to optical density ($OD_{600}$) equal to 0.5. The inoculum was concentrated to $2\times10^9$ CFUs/ml and 9 to 10 weeks old C3HeB/FeJ mouse is infected with 50 ul ($1\times10^8$ CFUs) of inoculum via oral aspiration. The inoculum CFUs was confirmed by plating on TSA plates and incubating overnight at 37° C.

Antibiotic Treatments:

RIF (Sigma, R3501-1G) and RBT (Sigma, R3530-25MG) were dissolved in Dimethyl sulfoxide (DMSO). The working solution of antibiotics are prepared fresh daily. The appropriate concentration of antibiotic working solution was prepared in PBS with 10% DMSO and administered by oral gavage. The control mice received the same volume of PBS with 10% DMSO without drug. RIF, RBT, and the control were administered once a day for three days starting the day of infection.

Blood CFUs:

50 to 100 ul blood was collected by tail nick at the indicated timepoints post OA or IV infection. Blood samples were serially diluted in PBS and plated on TSA plates. The plates are incubated overnight at 37° C. and CFUs were counted the next day.

Lung CFUs:

At 18 hrs post OA infection, lungs were harvested, weighed, and homogenized in sterile PBS. Lung homogenates were serially diluted in PBS and plated on TSA plates. The plates are incubated overnight at 37° C. and CFUs were counted the next day.

Statistics.

Bacterial burden was compared using the Mann Whitney test. Time to death was compared using the Log Rank test. P values<0.05 were considered significant.

Example 2

High Throughput Compound Screening-ReFRAME Library

The ReFRAME library is a curated small molecule library that represents over 10,000 compounds that cover small molecules with previously characterized activity, including antimicrobial activity [REF NEEDED]. The Inventors' primary goal was to identify novel compounds that were active against the Inventors' well characterized XDR, hyper-virulent clinical isolate of *A. baumannii* HUMC1 [FIG. 1]. However, the Inventors didn't want to miss potential hits that would be active against a less antibiotic-resistant target and therefore included a counter screen against the antibiotic susceptible ATCC 17978 strain. The Inventors selected RPMI to be used as the culture medium as it is less nutrient rich as compared to MHII. It has been previously reported that serum exposure induces gene expression changes in the bacteria and therefore serum was included to help simulate the bloodstream environment. The Inventors were concerned that any chemicals with high protein binding affinity would be missed during the screen so the Inventors also included an RPMI group without the addition of serum to model less stringent conditions. Lastly, the library was screened against mammalian cells to evaluate toxicity.

In total the Inventors screened 11,862 chemicals at 20 μM as an initial screen. The screen resulted in a hit rate of 0.52%; 62 putative hits were identified for follow up confirmation in a serial dose response screen. About half of the compounds (32/62) were validated to inhibit 50% of bacterial growth ($IC_{50}$) at a concentration of less than 20 μM. These compounds were also assessed for cytotoxicity and 4 compounds had a favorable specific activity ($IC_{50}$<20 μM) and low toxicity ($CC_{50}/IC_{50}$>10); of these rifabutin was the most potent (i.e., had the lowest MICs, Table 1).

Example 3

Rifabutin Vs Other Rifamycins

It was unexpected that RIF and RBT would have significantly different $IC_{50}$ values and the Inventors therefore tested a panel of 8 rifamycins to confirm activity using a more sensitive 11-point dose response curve. The Inventors evaluated the $IC_{50}$ against antibiotic-resistant and -susceptible *A. baumannii* strains in RPMI with and without serum (Table 2). Toxicity was also determined against 2 eukaryotic cell lines. RBT was confirmed to be the most potent and the most specific rifamycin tested (Table 2, 3).

Example 4

Confirmation of Rifabutin Activity by MIC

Figure 2:
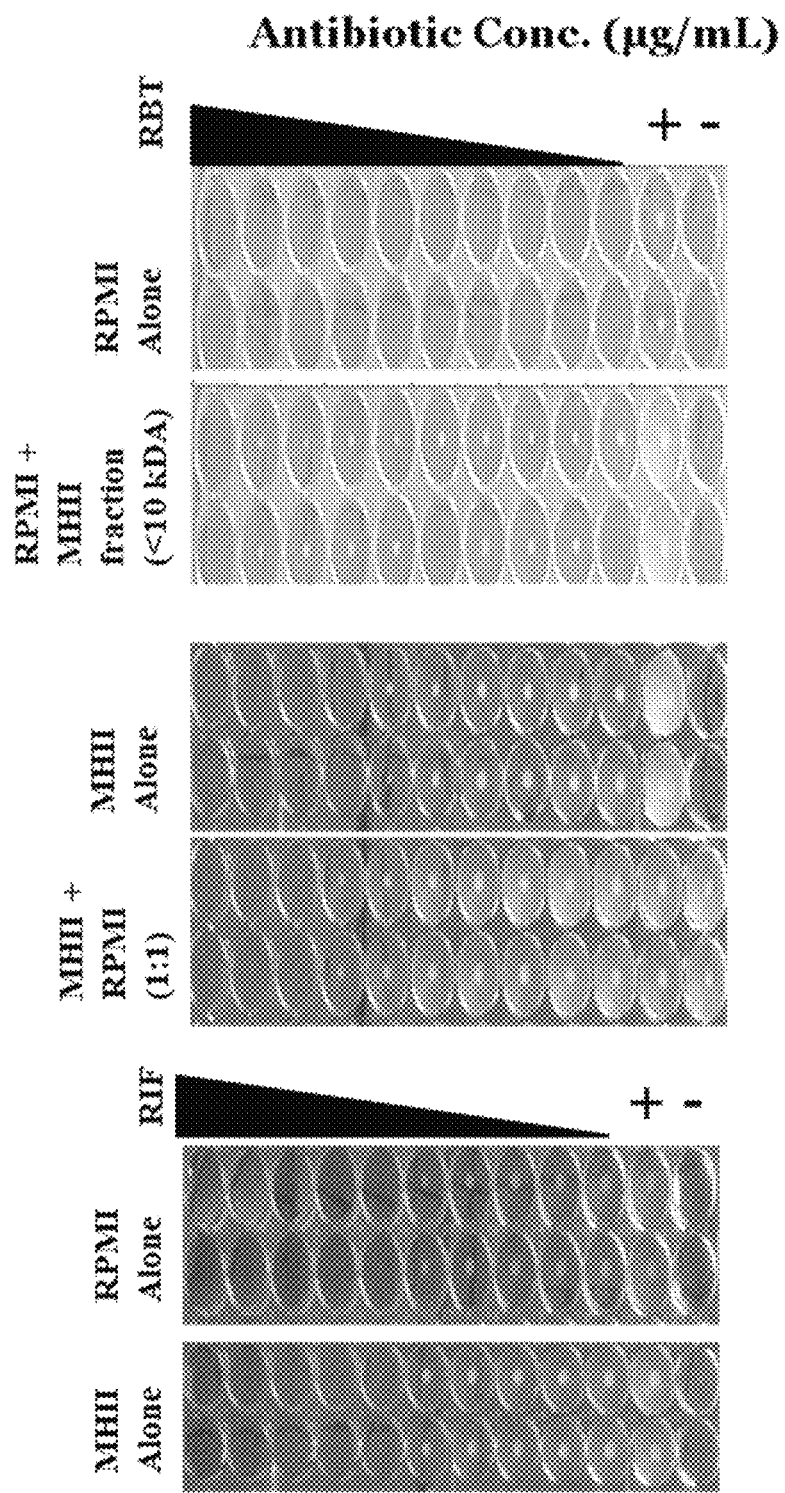
FIG. 2. MIC assays were done in either MHII alone, RPMI alone, or RPMI that was spiked MHII. MHII culture media was fractionated using molecular weight cutoff columns. The less than 10 kDa fraction inhibits the activity when spiked into RPMI media. MIC results from the above assays: RBT/RPMI<0.0625 µg/ml; RBT/RPMI+MHII Fraction=8 µg/ml; RBT/MHII=4 µg/ml; MHII+RPMI=8 µg/ml; RIF/RPMI=2 µg/ml; RIF+MHII=2 µg/ml.

The MIC of each antibiotic was determined using the broth microdilution method against *A. baumannii* HUMC1 and the Inventors were able to confirm the previously observed differences in activity from the chemical screen. In RPMI, the MIC of RBT (0.03 μg/mL) was 133-fold lower as compared to RIF (4 μg/mL) (FIG. 2). However, there was no difference in MIC when the bacteria were cultured in MHII (MIC=4 μg/mL for both RBT and RIF) (FIG. 2).

The Inventors also tested a panel of antibiotic susceptible or resistant isolates of *Staphylococcus aureus, Klebsiella pneumoniae*, and *E. coli* to determine if the decreased MIC observed in RPMI was generalizable to other bacteria. The Inventors did not find a universal improvement against other species tested (Table 4).

Example 5

MHII Vs RPMI Effects on RBT MIC

MHII Antagonizes RBT Activity

The Inventors mixed RPMI and MHII media in equal parts together and used this media to test the MIC. If the MHII media contained a component that antagonized RBT potency, the Inventors would expect that the MIC of RBT in hybrid RPMI-MHII media to be similar to the MIC of bacteria cultured in 100% MHII. In contrast, if the RPMI contained a component that promoted the activity RBT, then the Inventors would expect a MIC in the hybrid media to be closer to the MIC when the bacteria are cultured in 100% RPMI. The MICs of RBT was 4 and 8 μg/mL in the 100% MHII and hybrid media respectively (FIG. 2). This result suggested that the MHII media antagonized the activity of RBT.

Growth Rate

The Inventors sought to understand the drivers responsible for the change in RBT potency in RPMI versus MHII media. One possibility was that the bacteria grow more slowly when cultured in RPMI vs MHII, which could then slow down antimicrobial effect. Another way to slow bacterial grow is to alter the temperature of the cultures. However, the Inventors did not observe any difference in the RIF vs. RBT MICs when *A. baumannii* HUMC1 was cultured at lower temps of 25° C. or 30° C. compared to culture at the normal temp of 37° C. in MHII or RPMI. Therefore, the growth rate alone was not responsible for the differences in the observed antibiotic activity.

Carbon Source and Essential Nutrients

The primary carbon source in RPMI is glucose and the primary carbon source in MHII is proteins/peptides from the beef extract and casein digest. The Inventors evaluated if differences in central carbon metabolism was responsible to the observed differences in antibiotic activity by the Inventors spiking glucose into MHII at 1× and ⅒×the concentration present in RPMI. No difference in MIC was observed against *A. baumannii* HUMC1 in MHII with the different amounts of glucose added.

RPMI has less iron, an essential nutrient that is required for growth, as compared to MHII media contains an estimated 20 μg/mL compared to trace amounts present in RPMI. To recreate similar levels of iron in RPMI compared to MHII, $FeCl_3$ was spiked into RPMI at 0.01, 0.10, and 0.30 μg/mL and the MIC was evaluated. The addition of additional iron did not have any effect on the MIC of RBT against *A. baumannii* HUMC1.

MHII Fractions and Digested Products

The Inventors collected MHII media fractions based on size using molecular weight cutoff columns. The Inventors collected the <10 kDa fraction and spiked the fraction in RPMI media and again determined the MIC against RBT and RIF. The Inventors found that the addition of this fraction was sufficient to inhibit the activity of RBT (Table 5, FIG. 2).

The Inventors therefore focused on this low molecular weight fraction. The Inventors further separated the <10 kDa fraction by extracting the aqueous and organic phases by an acetonitrile liquid-liquid extraction. The addition of the purified aqueous layer to RPMI did not increase the MIC of RBT as observed in MHII. However, addition of the organic layer to RPMI did increase the MIC of RBT (Table 5). These results suggested that the material antagonizing RBT in MHII was protein-based.

If small molecular weight proteins or peptides present in MHII were the cause of the increase in MIC, the Inventors would expect that digestion of the proteins in the extracted organic layer would decrease the MIC to an equivalent value to that seen in RPMI. However, the Inventors did not observe a decrease in the MIC of RBT by treating the <10 kDa fraction with proteinase K (Table 5). If low molecular carbohydrate components present in MHII were the cause of the increase in MIC of RBT, the Inventors would expect that oxidation of carbohydrates by sodium periodate would reverse the effect. Just as with the proteinase K treatment, the Inventors did not observe a decrease in MIC or RBT upon the addition of sodium periodate treated <10 kDa MHII fraction (Table 5).

Lastly, the Inventors sought to determine the effect of free amino acids on the activity of RBT. The Inventors started by adding mixed amino acids (essential or nonessential) and found that addition of each mixture had an antagonistic effect on the activity of RBT (Table 5, 6). The Inventors then tested individual amino acids from the nonessential group to determine the contribution of each amino acid species and the Inventors found that RBT activity was inhibited by the addition of L-histidine and L-tryptophan (Table 6).

Example 6

In Vivo RBT Activity

The Inventors next evaluated if the potent activity of RBT would translate to enhanced efficacy vs. RIF in in vivo mouse models of disease. The Inventors first tested the efficacy of the RBT vs. RIF in an *A. baumannii* pneumonia model. Mice were infected with *A. buamnannii* HUMC1 and treated with treated with 10/mg/kg/day RIF or RBT for 3 days. At 24 hours, RBT-treated mice had a 7-log reduction in the median CFUs in the blood as compared to RIF-treated mice. There was a modest improvement in survival as well. (FIG. 3A-B).

The Inventors repeated the experiment with a reduced dose of each drug to determine if the efficacy difference would be enhanced (presuming greater potency of RFB vs. RIF). Mice were infected and treated with 5 mg/kg/daily of either drug or placebo for 3 days, and lungs were harvested and the bacterial density of the organs was quantified. RBT-treated mice had significantly reduced lung CFUs and significantly improved survival (FIG. 3C-D). Mice that were treated with 5 mg/kg of RIF did not do any better as compared to the PBS control group. This experiment validated the initial mouse experiment and the Inventors' hypothesis that RBT is more potent in vivo as compared to RIF.

Figure 4:
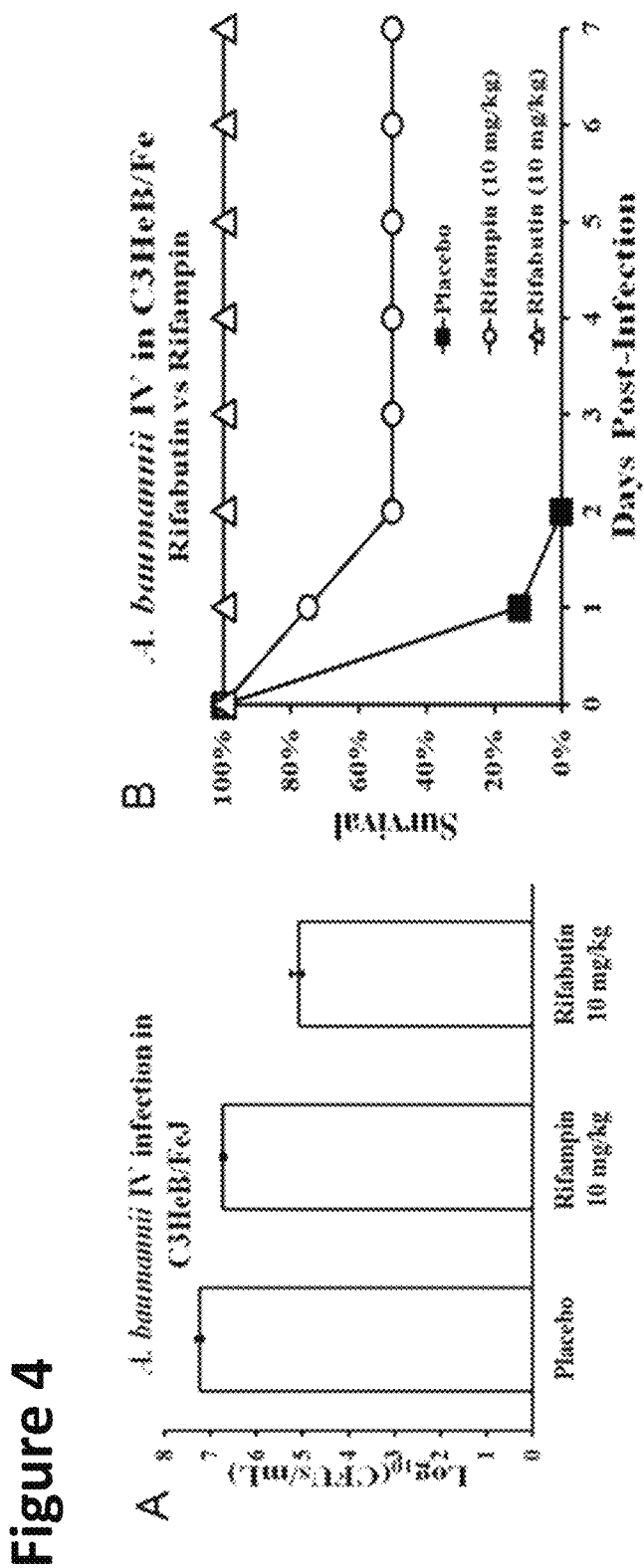
FIG. 4. RBT vs RIF therapy in an *A. baumannii* IV infection mouse model. C3H mice (n=8) were A) infected with via tail vein injection with *A. baumannii* HUMC1 (antibiotic-resistant strain) and mice were treated with 10 mg/kg/daily for 3 days with B) RIF or RBT by oral gavage. Blood was collected at 24 hrs from mice (n=8) and serial dilutions were plated to determine the bacterial density. Mice that received the rifabutin treatment had significantly lower CFUs in the lung at 24 hrs post infection and also improved survival.
Figure 5:
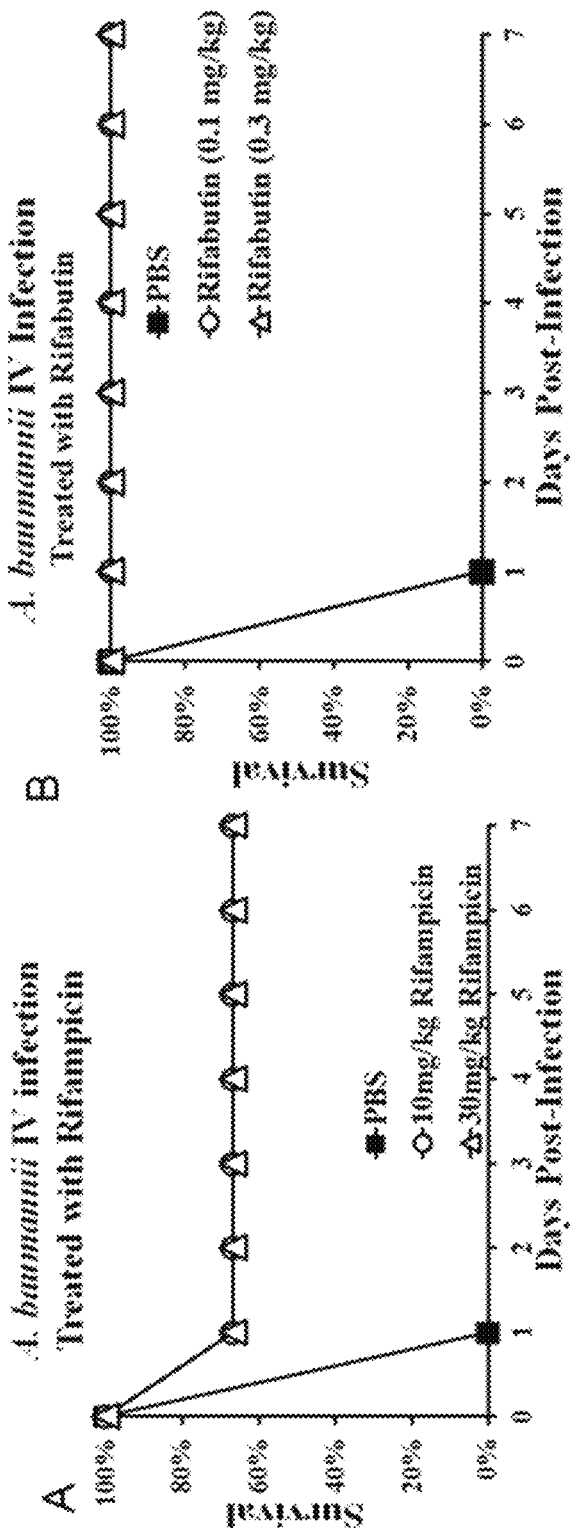
FIG. 5. RBT vs RIF therapy in an *A. baumannii* IV infection mouse model. C3H mice were A) infected with *A. baumannii* HUMC1 and mice were B) treated with 10 or 30 mg/kg/daily for 3 days with RIF; or mice were treated with 0.1 or 0.3 mg/kg/daily for 3 days with RBT by oral gavage. RBT was fully protective at doses that were 100× lower that RIF.
Figure 6:
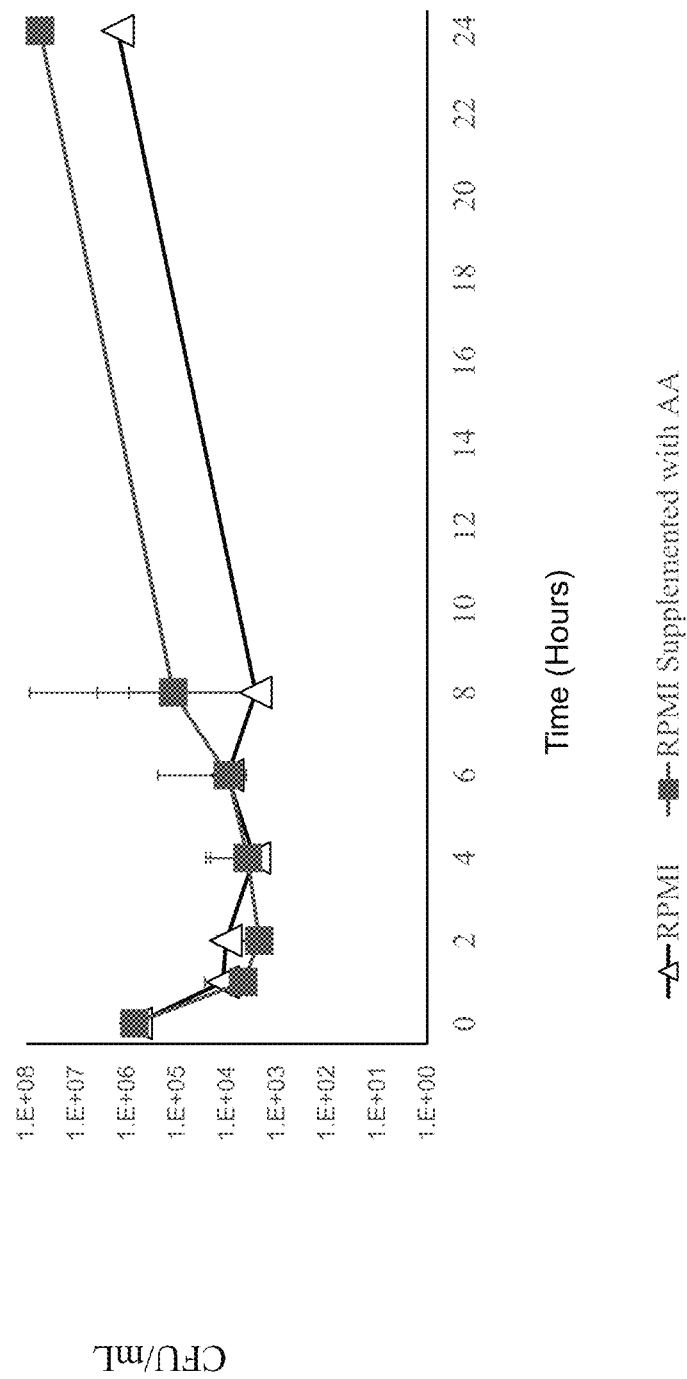
FIG. 6. Time kill assay. An overnight culture of *A. baumannii* HUMC1 was subcultured in fresh RPMI, with or without supplemented amino acids, and the number of viable cells was determined by plating serial dilutions at 0, 1, 2, 4, 6, 8, and 24 hours.

Next the Inventors tested if RBT was more effective than RIF in an intravenous model of infection. Mice were infected IV with HUMC1 and treated with 10/mg/kg/day RIF or RBT for 3 days. At 24 hours, RBT-treated mice had significantly lower CFUs in the blood as compared to RIF-treated mice. Additionally, there was also a significant improvement in survival as well. (FIG. 4). Lastly, the Inventors tested with the minimum dose required for RBT or RIF would allow for protection in an IV infection model. The Inventors found that RBT was fully protective when dosed at 100× lower concentration as compared to RIF which was only partially protective (FIG. 5)

TABLE 1

Specificity results from the top hits of the chemical screen.

| Compound | Specificity HEK293T (CC50/IC50) | Specificity HepG2 (CC50/IC50) |
| --- | --- | --- |
| CBR-001-573-826-8 (rifabutin) | 148.31 | 148.31 |
| CBR-001-634-681-9 | 10.44 | 25.61 |
| CBR-001-573-317-2 | 14.02 | 14.02 |
| CBR-001-634-178-9 | 13.82 | 13.82 |

The IC50 value represents testing against *A. baumannii* HUMC1 in 50% serum. Rifabutin was the most active of the compounds identified.

TABLE 2

IC50 [μM] of 8 rifamycins against *A. baumanttii*.

| | RPMI | | RPMI + 50% Serum | |
| --- | --- | --- | --- | --- |
| Compound | ATCC 17978 | HUMC1 | ATCC 17978 | HUMC1 |
| rifabutin | 0.024 | 0.001 | <0.000847 | <0.000847 |
| rifaximin | 1.777 | 1.526 | 2.449 | 1.586 |
| rifapentine | 7.589 | 10.043 | 28.060 | 10.889 |
| FCE-22250 | 9.738 | 9.034 | 35.294 | 21.697 |
| rifampicin | 13.808 | 11.018 | 18.245 | 7.993 |
| rifalazil | 17.384 | 20.004 | 50.000 | 7.510 |
| rifamycin | 28.431 | 20.793 | 33.023 | 35.442 |
| rifamycin SV | 45.147 | 37.095 | 50.000 | 50.000 |

An 11-point dose response curve was used to determine activity. Rifabutin was significantly more active as compared to rifamycins tested.

TABLE 3

Specificity results of the rifamycins against *A. baumanni*

| | HEK293T (CC50/IC50) | | | |
|---|---|---|---|---|
| | RPMI alone | | RPMI + 50% serum | |
| Compound | ATCC 17978 | HUMC1 | ATCC 17978 | HUMC1 |
| rifabutin | 1961.478 | 33559.242 | 506006.298 | 97331.320 |
| rifaximin | 28.143 | 32.776 | 20.421 | 31.517 |
| rifapentine | 4.517 | 3.413 | 1.222 | 3.148 |
| rifampicin | 3.621 | 4.538 | 2.741 | 6.256 |
| FCE-22250 | 3.441 | 3.710 | 0.950 | 1.545 |
| rifalazil | 1.752 | 1.523 | 0.609 | 4.055 |
| rifamycin SV | 1.108 | 1.348 | 1.000 | 1.000 |
| rifamycin | 0.478 | 0.654 | 0.412 | 0.383 |

Rifabutin was the most active rifamycin and also displayed low toxicity against eukaryotic cells.

TABLE 4

MICs were performed for various strains of bacteria
Various Strains MIC (µg/mL)

| | | Rifabutin | Rifampin |
|---|---|---|---|
| *A. baumannii* HUMC1 | MHII | 3.125 | 3.125 |
| | RPMI | 0.0156 | 3.125 |
| *A. baumannii* VA-AB21 | MHII | 3.125 | 3.125 |
| | RPMI | 0.391 | >6.125 |
| *S. aureus* LAC | MHII | 0.012 | 0.025 |
| | RPMI | 0.025 | 0.05 |
| *K. pneumonia* KPC-KP1 | MHII | 25 | 25 |
| | RPMI | 12.5 | 50 |
| *K. pneumonia* KP-3 | MHII | 1.56 | 3.125 |
| | RPMI | 0.391 | 1.56 |
| *E. coli* JJ1886 | MHII | 6.25 | 6.25 |
| | RPMI | 6.25 | 25 |
| *E. coli* DH5a | MHII | 6.25 | ND |
| | RPMI | ND* | ND |

MICs were performed for various strains of bacteria to determine if effect seen with rifabutin between MHII and RPMI is a strain-specific phenomenon or a common effect between multiple strains.

TABLE 5

MICs were performed for against HUMC1 using with rifabutin in RPMI
*A. baumannii* HUMC1 MIC (µg/mL)

| | Rifabutin | Rifampin |
|---|---|---|
| Media Controls | | |
| MHII | 3.125 | 3.125 |
| RPMI | 0.0156 | 3.125 |
| Modified RPMI | | |
| 5X RPMI | <0.0625 | ND |
| RPMI Supplemented with MHII | 8 | ND |
| Fractionated MHII Spiked Into RPMI | | |
| 10-30 kDa MHII Fraction | 8 | ND |
| <10 kDa MHII Fraction | 8 | ND |
| Acetonitrile Treated <10 kDa MHII Fraction | | |
| Aqueous Layer | <0.0312 | ND |
| Organic Layer | 4 | ND |
| Organic Layer, Proteinase K Digested | 4 | ND |
| Organic layer, Sodium Periodate Treated | 4 | ND |
| Essential Amino Acid Solution (50X) | | |
| MHII | ND | ND |
| RPMI | 1.56 | 6.25 |
| Non-Essential Amino Acid Solution (100X) | | |
| MHII | 3.125 | ND |
| RPMI | 0.781 | ND |
| Efflux Pump Inhibitor | | |
| CCCP (2 µg/mL) | <.05 | |
| CCCP (2 µg/mL) + Essential Amino Acids | 1.56 | |
| Detergents | | |
| 0.05% Tween 20, MHII | | 2 |
| 0.01% Triton X-100 | | 2 |
| Culture conditions | | |
| Tissue culture treated 96-well plates | 1.56 | |
| Non tissue culture treated 96-well plates | 1.56 | |
| 25° C., RPMI | <.06 | 2 |
| 25° C., MHII | 4 | 2 |
| Culture Media | | |
| No Salt Luria Broth | 1 | |
| Low Salt Luria Broth | 2 | |
| Luria Broth | 1 | |
| M9 | <0.05 | |
| MHII | 3.125 | 3.125 |
| RPMI | 0.0156 | 3.125 |

MICs were performed for against HUMC1 using with rifabutin in RPMI, unless otherwise indicated on the table, to determine which component of MHII inhibits the activity of rifabutin. The MIC for CCCP alone is 8 µg/mL

TABLE 6

MICs were performed to determine if an increase in MIC will result by the the addition of individual amino acids to the MIC.
9999999Amino Acid MIC (µg/mL)

| | | Final Concentration/Well (mM) | Rifabutin | Rifampin |
|---|---|---|---|---|
| Controls | RPMI Only | ND | 0.0156 | 3.125 |
| | MHII Only | ND | 3.125 | 3.125 |
| Amino Acid | L-Arginine | 0.5 | <0.048 | ND |
| | Glutamic Acid | 0.5 | <0.048 | ND |
| | Glycine | 0.5 | <0.048 | ND |
| | L-Histidine | 0.5 | 1.56 | 12.5 |
| | Leucine | 1 | <0.048 | ND |
| | L-Tryptophan | 0.125 | 1.56 | 12.5 |

MICs were performed to determine if an increase in MIC will result by the the addition of individual amino acids to the MIC.

TABLE 7

Mutation Frequencies.
RIF and RBT Mutation Frequency

| | TSA | | MHII | |
|---|---|---|---|---|
| Strain | Rifabutin | Rifampin | Rifabutin | Rifampin |
| *A. baumannii* HUMC1 | 1.28E-08 | 1.44E-08 | 2.20E-09 | 9.19E-09 |
| *A. baumannii* ABNIH1 | 5.95E-09 | 1.75E-08 | 8.85E-09 | 4.17E-08 |

TABLE 7-continued

Mutation Frequencies.
RIF and RBT Mutation Frequency

| Strain | TSA | | MHII | |
|---|---|---|---|---|
| | Rifabutin | Rifampin | Rifabutin | Rifampin |
| A. baumannii ATCC117978 | 8.49E−10 | 7.95E−09 | 5.72E−09 | 5.14E−09 |
| A. baumannii LAC-4 | 7.41E−09 | 1.76E−08 | 1.29E−08 | 2.62E−08 |
| S. aureus LAC | 1.10E−07 | 9.49E−08 | | |
| E. coli JJ1886 | 3.89E−08 | 2.21E−08 | | |

The mutation frequency was found to be similar between RBT and RIF when the bacteria were cultured on TSA and MHII agar plates. The frequency of resistance to either drug was found to be lower as compared to S. aureus and E. coli.

TABLE 8

Rifabutin MICs against A. baumannii AB5075 transposon disruption mutants deficient in amino acid transport genes.

| Strain | Disrupted Gene | MHII (µg/mL) | RPMI (µg/mL) |
|---|---|---|---|
| HUMC1 | | 6.25 | <0.05 |
| AB5075-UW | | 6.25 | <0.05 |
| AB00188 | aroP | 3.13 | <0.05 |
| AB00190 | aroP | 6.25 | <0.05 |
| AB03015 | aroP | 6.25 | <0.05 |
| AB02204 | aroP | 6.25 | <0.05 |
| AB09979 | aroP | 0.78 | <0.05 |
| AB09980 | tryP | 3.13 | <0.05 |
| AB00215 | tryP | 6.25 | <0.05 |
| AB03612 | hisM | 3.13 | <0.05 |
| AB03616 | hisM | 6.25 | <0.05 |
| AB03618 | hisM | 6.25 | <0.05 |
| AB06383 | hisJ | 6.25 | <0.05 |
| AB07813 | mtr | 25 | <0.05 |
| AB02205 | aroP | 3.13 | <0.05 |
| AB07354 | aroP | 6.25 | <0.05 |
| AB07356 | aroP | 1.56 | <0.05 |
| AB09982 | tryP | 6.25 | <0.05 |
| AB00216 | tryP | 1.56 | <0.05 |
| AB06392 | hisP | 0.78 | <0.05 |
| AB06386 | hisP | 0.78 | <0.05 |
| AB06105 | aroP | 3.13 | <0.05 |
| AB03608 | hisJ | 3.13 | <0.05 |

Rifabutin MICs against A. baumannii AB5075 transposon disruption mutants deficient in amino acid transport genes. MIC assay was done by culturing the bacteria in either MHII or RPMI media.

Example 7

Discussion

A. baumannii is one of the few bacteria strains of which have developed resistance to all available antibiotics. National surveillance data confirm that an astonishing 50% of A. baumannii isolates from US intensive care units are XDR, far higher than for other pathogens, including Pseudomonas aeruginosa (20%) or Klebsiella spp. (10%).[1,2] Approximately 23,000 and 75,000 cases of XDR A. baumannii infections occur annually in the US and globally (in developed countries), respectively.

High throughput chemical screening assays have been a standard practice for the pharmaceutical industry for decades. However, these libraries have been screened many times, and rarely do new screens of the same library identify novel compounds that have not been previously identified. One fundamental limitation is that the culture conditions will influence the physiologic state of the bacteria. A change in cellular physiology could alter the availability of the drug target or affect drug metabolism. This may result in a culture-dependent susceptible phenotype that selects for false positives or a resistant phenotype that selects for false negatives. Changes in the carbon source during culture can result in significant overall changes in both gene expression and protein translation. These metabolic changes have been shown to have direct effects on antibiotic activity. A significant amount of time, labor, and financial resources may have been lost to the characterization of drug candidates that target a metabolic process that is active in vitro but not in vivo.

The modification of in vitro culture conditions to best reflect in vivo conditions are needed for the best chance of success. For example, some pathogens, such as Mycobacterium tuberculosis (M. tb), are likely to reside in host macrophages which constitute a significantly different environment as compared to nutrient rich broth culture of the bacteria alone. Modified screening protocols that involved screening chemicals against M. tb infected macrophages resulted in the identification of novel compounds. To identify rifabutin, the Inventors modified the culture conditions to better reflect the in vivo environment of a bloodstream infection by culturing the bacteria in a relatively nutrient depleted media with the addition of serum. The Inventors found that RFB was much more potent than RIF when tested in the depleted media plus serum but not in rich media. Validating the relevance of this approach is that RFB was also more effective in vivo when treating mice infected intravenously or with pneumonia caused by an XDR hypervirulent clinical isolate of A. baumannii. This finding would not have been made had the initial screen been conducted with rich media.

The relative superiority of RFB over RIF is highly significant due to a recent, randomized, controlled clinical trial that found a non-significant trend to improved clinical cure, with a significant improvement in microbiological eradication when adding rifampin to colistin for treatment of XDR A. baumannii infections. Given that RIF had some effect clinically, and that RFB appears far more potent and effective in pre-clinical models, the Inventors believe that the addition of adjunct RFB, as compared to RIF, could serve as a critically needed new therapeutic option for patients with infections caused by XDR A. baumannii, potentially resulting in superior survival compared to the current standard of care. As RBT is already commercially available, these results can be immediately translated.

Example 8

Additional Materials and Methods

Bacteria Culture

Working solutions of bacteria were prepared using frozen stocks of Acinetobacter baumannii, Klebsiella pneumonia, and Staphylococcus aureus strains as previously published,[12] or by inoculating a fresh overnight culture in Tryptic Soy Broth (TSB) and incubating at 37° C./200 rpm. The overnight culture was diluted 1:100 and then subcultured in MHII at 37° C./200 rpm until the culture reached an $OD_{600}$ of 0.5.

High Throughput Compound Screening

Compounds from the 10 mM ReFRAME library stock were pre-spotted at 20 µM final assay concentration into 384 or 1536 well plates. Log-phase growth *A. baumannii* HUMC1 was be diluted in assay media (MHII or RPMI with and without 50% mouse serum) and dispensed into assay plates. Bacterial viability was assessed 24 hours later using the BacTiter-Glo Microbial Cell Viability Assay. Positive controls included 10 μM colistin and doxycycline. Assay was normalized to neutral and inhibitor controls and putative hits were be selected based on 50% reduction in viability. Putative hits were re-tested in single point triplicate and upon reconfirmation were further tested in an 8 point 1:3 dose response and counter-screened against mammalian HepG2 and HEK293T cell lines. Dose response synergy testing was done to follow up on hits that appear to potentiate activity of meropenem (10 μM) with the goal of identifying compounds that increase meropenem $EC_{50}$ at least 100-fold (MIC difference between the resistant HUMC1 and susceptible ATCC17978 strain is ~128).

Antibiotic Preparation

RIF (Sigma, R3501-1G) and RBT (Sigma, R3530-25MG) were dissolved in Dimethyl sulfoxide (DMSO). The working solution of antibiotic was prepared 2× of the desired starting well final drug concentration. The antibiotic working solution dilutions were prepared in the respective media used for the MIC, MHII or RPMI.

MIC Protocol

Unless otherwise indicated, the standard broth microdilution method was used to determine MICs. The medium used for the minimum inhibitory concentration (MIC) assays performed in this study was either MHII or RPMI 1640.

Briefly, 100 μl of media, RPMI or MHII, was added to the wells in columns 2-10. Column 11 served as a positive growth control and contained only bacteria and media. Column 12 served as the negative control and contained only culture media without bacteria. Next, 200 μl of a 2× rifabutin or rifampin working solution was added to the wells in column 1. Two-fold serial dilutions of the antibiotic were performed through column 10. Next, 100 μl of a 1×10⁶ CFU/mL working solution of bacteria was added to each of the wells in columns 1-11. The inoculum concentration was confirmed by plating serial dilutions on TSA plates. MICs plates were incubated at 35±2° C. without shaking and results were recorded at 24 hours.

To test the effect of the individual components of MHII, MHII fractions (size separation, acetonitrile extracted, proteinase K digested, or sodium periodate oxidized), 10 μL of the purified fraction was added to the appropriate wells.

As indicated, amino acids were used to supplement the media for MIC testing. Mixed amino acids were tested by adding 10 μL of Gibco® MEM Amino Acids Solution (Thermo Scientific, #11130051) and Gibco® MEM Non-Essential Amino Acids (Thermo Scientific, #11140050) to each well in the MIC assay. Additionally, the effect of individual amino acids on the MIC was tested by the addition of purified amino acids at the same concentration contained in the Gibco mixed amino acid solutions listed above. Amino acids were prepared fresh and filter sterilized solutions prior to use.

For some MICs, efflux pump inhibitors were added to the media. Efflux pump inhibitor MICs were performed to identify subinhibitory concentrations of the efflux pump inhibitors. The final concentration of inhibitors used were as follows: verapamil (100 μg/mL), thioridize (16 μg/mL), arsenate (33.3 mM), and CCCP (2 μg/mL).

Fractionation of MHII:

Size Fractionation

10×MHII was used for the fractionation to maximize the concentration of the MHII components. The media was filtered through a 0.22 μM filter and then the media was run through 10 and 30 kDa molecular weight cut-off (MWCO) centrifugal filtration columns at 12,000 g for 20 minutes. The >30 kDa fraction was collected and reserved for experimentation. The flow through was collected and transferred to a 10 kDa MWCO column. The centrifugation step was repeated as previously stated. The <10 kDa flow through was collected from this column. The 10<X<30 kDa fraction was collected as well.

Acetonitrile Extraction

The organic and inorganic layers were separated with a liquid-liquid extraction by mixing the purified MHII fraction 1:1 with 100% acetonitrile. The sample was vortexed thoroughly and centrifuged at maximum speed for 10 minutes. The aqueous and organic layers were transferred to clean microcentrifuge tubes. To ensure the removal of any residual acetonitrile, the extracted MHII sample was dried using a SpeedVac and then resuspended in the original volume using sterile molecular grade H2O.

Proteinase K Digestion

30 μl of proteinase K (Invitrogen, #46-7603) was added to 1 mL of the MHII<10 kDa fraction (organic extract or non-extracted as a control). The media was incubated at 65° C. for 1 hour. To inactivate the proteinase K, the sample was then incubated at 80° C. for 15 minutes.

Sodium Periodate Oxidation

Sodium periodate oxidation was done as previously described.[13] Briefly, to oxidize the carbohydrates in the organic layer of the medium, sodium periodate (NaIO4) was added to the <10 fraction at a final concentration of 10 mM. The sample was incubated at room temperature for 30 minutes. Following incubation, the sodium periodate was quenched using 0.1 mL of 50% glycerol for every 1 mL of reaction. The sample was incubated at room temperature for 1 hour before downstream application.

Time Kill Assay

Time kill assays were performed in a 96-well U-bottom plate using the same plate set up as the MIC assay. The Inventors measured viable cell counts at 1, 8, and 24 hours. At each time point, the contents of the an individual well were collected and CFUs were determined by plating serial dilutions on TSA plates and incubating overnight at 37° C.

As a control, the remaining wells of the 96-well plate were returned to the incubator after each sample collection and an MIC was determined as described above.

Mass Spectrophotometry

Log-phase *A. baumannii* culture was incubated 0.79 or 0.38 μg/mL RBT in the presence or absence of amino acid mixture at 37° C. Bacteria were harvested 0, 1, 8, and 24 hours and CFUs were determined by plating serial dilutions on agar media. The cell free supernatant was collected by filtration through a 0.22 μm filter. RBT were extracted by adding LC-MS grade acetonitrile:methanol:water (40:40:20) solution that was precooled to −40° C. Liquid chromatography mass spectrometry (LC-MS) differentiation and detection of RBT was performed using a Cogent Diamond Hydride Type C column (Microsolve Technologies) with an Agilent Accurate Mass 6230 TOF coupled with an Agilent 1290 Liquid Chromatography system as previously published.[14,15] An isocratic pump was used for continuous infusion of a reference mass solution to allow mass axis calibration. Detected RBT ion was validated based on unique accurate mass-retention time identifiers for masses. RBT level was analyzed using Agilent Qualitative Analysis B.08.00 (Agilent Technologies) with a mass tolerance of <0.005 Da. The intracellular RBT was calculated as the [RBT]$_{drug\ only\ control}$-[RBT]$_{filtrate}$. 3 biological replicates were tested per group.

Selection of Spontaneous RBT-Resistant Mutants and WGS:

The RBT hypersensitive strain HUMC1 was cultured overnight in TSB. Bacteria were plated on RPMI agar plates supplemented with 3 µg/mL of RBT. Individual colonies were selected and then counter screened in RPMI agar plates supplemented with 25 µg/mL RBT.

Colonies that grew on the RPMI agar plates supplemented with 3 µg/mL, but not the 25 µg/mL RBT, were processed for whole genome sequencing. Selected mutants, and the parent strain, were Sequencing libraries for the selected mutants and parent strain were prepared at the USC Molecular Genomics Core. Libraries were simultaneously prepared from extracted genomic DNA using the Illumina Nextera XT library prep kit according to the manufacturer's protocol (Cat #FC-131-1024, Illumina). Prepared libraries were sequenced on the Illumina Miseq V2 at 2×150 cycles. Assembled reads were aligned to the previously published *A. baumannii* HUMC1 sequence (NCBI Reference Sequence: NZ LQRQ01000007.1).

Mouse Studies

Intravenous (IV) Infection

*A. baumannii* HUMC1 frozen stock was prepared as described in previous work.[12] Frozen stocks of HUMC1 were thawed and diluted in PBS to adjust the bacterial density as needed for infection. C3HeB/FeJ mice, 8 to 14 weeks old, were infected with 2×10$^7$ CFUs via tail vein injection and the inoculum bacterial density was confirmed by plating serial dilutions on TSA plates and incubating overnight at 37° C.

Oral Aspiration (OA) Infection

Single colonies of *A. baumannii* HUMC1 grown on TSA were used to inoculated TSB and bacteria were cultured overnight at 37° C./200 rpm. The following day, the bacteria was subcultured by diluting the overnight 1:100 in fresh TSB and cultured for 3 hrs at 37° C./200 rpm. The subculture was washed with PBS three times and adjust to optical density (OD$_{600}$) equal to 0.5. The inoculum was concentrated to 2×10$^9$ CFUs/ml and 9 to 10 weeks old C3HeB/FeJ mouse is infected with 50 ul (1×10$^8$ CFUs) of inoculum via oral aspiration. The inoculum CFUs was confirmed by plating on TSA plates and incubating overnight at 37° C.

Antibiotic Treatments

RIF (Sigma, R3501-1G) and RBT (Sigma, R3530-25MG) were dissolved in Dimethyl sulfoxide (DMSO). The working solution of antibiotics are prepared fresh daily. The appropriate concentration of antibiotic working solution was prepared in PBS with 10% DMSO and administered by oral gavage. The control mice received the same volume of PBS with 10% DMSO without drug. RIF, RBT, and the control were administered once a day for three days starting the day of infection.

Blood CFUs 50-100 µL of blood was collected by tail nick at the indicated timepoints post OA or IV infection. Blood samples were serially diluted in PBS and plated on TSA plates. Agar plates were incubated overnight at 37° C. and CFUs were counted the next day.

Lung CFUs

At 18 hrs post infection, lungs were harvested, weighed, and homogenized in sterile PBS. Lung homogenates were serially diluted in PBS and plated on TSA plates. The plates are incubated overnight at 37° C. and CFUs were counted the next day.

Statistics

Bacterial burden was compared using the Mann Whitney test. Time to death was compared using the Log Rank test. P values<0.05 were considered significant.

Example 9—High Throughput In-Vitro Chemical Screen 1.1 Initial Chemical Screen

A high throughput chemical screen was conducted in which compounds (in a concentration of 20 mM) were assessed for their ability to inhibit *A. baumannii* growth in a 1536 well format.

1.1.1 Bacteria Culture

Single colonies from agar plates were picked to inoculate 10 mL broth cultures in TSB media. Bacteria were cultured overnight at 37° C. with shaking at 200 rpm. A fresh subculture was by inoculating 100 µL of the overnight culture into 10 mL of fresh TSB media, and incubated at 37° C. with shaking at 200 rpm for 3 hours. Bacteria were washed 3× with PBS and the OD$_{600}$ density was adjusted. Bacteria were diluted in either RPMI or MHII medium, with or without the addition of 50% serum. MHII is the standard reference culture medium that is used by clinical laboratories for determining antibacterial activity by the MIC assay. RPMI was included as model of in vivo environmental conditions. Viability of the bacteria was monitored and quantified using the BacTiterGlo.

1.1.2 Sample Analysis

Fluorescence was measured after 24 hours of incubation. Background wells containing only media were subtracted from other test wells. The % of inhibition by the compounds was normalized to growth control well that contained no inhibitor compound. The IC50 was determined as the concentration of compound that provided a 50% inhibition relative to the untreated growth control.

1.1.3 Results 11,862 compounds were screened and rifabutin was identified as the most potent inhibitor of *A. baumannii* growth.

1.2 Minimum Inhibitory Testing 1.2.1 MIC Testing of Rifampin and Rifabutin Against *A. baumannii* in RPMI or MHII As a secondary confirmation of the primary high throughput screen results, MIC of rifampin (RIF) and rifabutin (RBT) against *A. baumannii* cultured in RPMI or MHII was determined.

1.2.2. MIC Plate Set Up

The bacteria were cultured the same as described above. A series of two-fold serial dilutions of RBT or RIF were done in 96-well plates. The drugs were diluted in RPMI or MHII respectively. Bacteria were added and the plates were incubated for 24 hours at 37° C. *A. baumannii* infections 1.2.3 Sample Analysis The MIC is defined as the lowest concentration of drug in which there is no visible growth of bacteria.

1.2.4 Results

Against *A. baumannii* ATCC17978 and HUMC1, the MIC of RIF and RBT in MHII were both 2 µg/mL. In RPMI, the MIC of RBT was <0.0625 µg/mL and RIF was 8 µg/mL.

1.2.5 IC$_{50}$ Testing of Rifamycin Compounds

The IC$_{50}$ was determined for eight rifamycin compounds (members of the rifamycin family) using an 11-point dose response curve to determine activity. RBT was found to be the most potent against both HUMC1 and ATCC17978 (Table 9).

TABLE 9

IC$_{50}$ [μM] of 8 members of the Rifamycin family against *A. baumannii*

| Compound | 'ATCC 17978 in RPMI | HUMC1 in RPMI | ATCC 17978 in RPMI + 50% Serum | HUMC1 in RPMI + 50% serum |
|---|---|---|---|---|
| rifabutin | 0.024 | 0.001 | <0.000847 | <0.000847 |
| rifaximin | 1.777 | 1.526 | 2.449 | 1.586 |
| rifapenline | 7.589 | 10.043 | 28.060 | 10.889 |
| FDE-22250 | 9.738 | 9.034 | 35.294 | 21,697 |
| rifampicin | 13.808 | 11.018 | 18.245 | 7.993 |
| rifalazil | 17.384 | 20.004 | 50.000 | 7.510 |
| rifamycin | 28.431 | 20.793 | 33.023 | 35.442 |
| rifamycin SV | 45.147 | 37.095 | 50.000 | 50.000 |

In a test of 21 clinical isolates of *A. baumannii*, intrinsic resistance to rifabutin and rifampin was found in one strain (Table 2). Of the 20 non-resistant strains, 15 demonstrated markedly lower MICs to rifabutin in RPMI medium than in MHII media (Table 10).

TABLE 10

Rifabutin MICs of clinical isolates of *A. baumannii* in RPMI or MHII Media

| | *A. baumannii* Strain | Media | Rifabutin |
|---|---|---|---|
| 1 | HUMC1 | MHII | 3.125 |
|   | HUMC1 | RPMI | 0.0156 |
| 2 | ATCC 17978 | MHII | 3.125 |
|   | ATCC 17978 | RPMI | <0.05 |
| 3 | VA-AB21 | MHII | 3.125 |
|   | VA-AB21 | RPMI | 0.391 |
| 4 | ARLG-1915 | MHII | 3.13 |
|   | ARLG-1915 | RPMI | 0.1 |
| 5 | UH6507 | MHII | 3.13 |
|   | UH6507 | RPMI | 0.39 |
| 6 | HUMC6 | MHII | 25 |
|   | HUMC6 | RPMI | 3.13 |
| 7 | HUMC10 | MHII | 12.5 |
|   | HUMC10 | RPMI | <0.05 |
| 8 | ARLG-1314 | MHII | 6.25 |
|   | ARLG-1314 | RPMI | <0.05 |
| 9 | AB15827 | MHII | 3.13 |
|   | AB15827 | RPMI | 0.2 |
| 10 | AB307-0294 | MHII | 6.25 |
|    | AB307-0294 | RPMI | <0.05 |
| 11 | LACUSC-01 | MI-III | 6.25 |
|    | LACUSC-01 | RPMI | <0.05 |
| 12 | U H118 | MHII | 3.13 |
|    | UH118 | RPMI | 0.2 |
| 14 | AB046 | MHII | 6.25 |
|    | AB046 | MHII | 0.19 |
| 15 | AB044 | MHII | 3.12 |
|    | AB044 | RPMI | 0.78 |
| 16 | UH516 | MHII | >25 |
|    | U H516 | RPMI | >25 |
| 17 | VA-AB74 | MHII | 6.25 |
|    | VA-AB74 | RPMI | 3.13 |
| 18 | ARLG-1777 | MHII | 6.25 |
|    | ARLG-1777 | RPMI | 3.13 |
| 19 | NIH1 | MHII | 3.13 |
|    | NIH1 | RPMI | 3.13 |
| 20 | UH2207 | MHII | 6.25 |
|    | UH2207 | RPMI | 3.13 |
| 21 | LAC--4 | MHII | 0.78 |
|    | LAC--4 | RPMI | 1.56 |

Example 10

In Vivo Animal Efficacy Studies

It was determined if the MIC assay results in RPMI or MHII were more predictive of in vivo efficacy, and efficacy of rifampin and rifabutin as therapy for *A. baumannii* infections in mice was compared.

Mouse and Bacterial Strains: C3H/FeJ mice were used for all animal studies. *A. baumannii* HUMC1, a highly virulent, XDR clinical blood and lung isolate, was used for all animal infections.

3.1 Oral Aspiration Pneumonia Infection Model

Frozen stocks of *A. baumannii* HUMC1 were thawed prior to infection and the CFU density was adjusted to deliver a targeted inoculum of $2 \times 10^8$ CFU per mouse for the aspiration pneumonia route. Mice were anesthetized with isofluorane, the mouse tongue grasped to prevent swallowing, and infectious inoculum was administered in 50 μl of PBS directly into the trachea. Following infection, mice were treated by oral gavage for 3 days with freshly prepared RIF or RBT resuspended in 10% DMSO. Treatment dosing was 5 or 10 mg/kg once per day depending on the experiment.

3.1.1 Sample Analysis

Treatment efficacy was evaluated based on survival time and the reduction in bacterial CFUs. Bacterial density was measured by collecting blood or lung tissue and plating serial dilutions on agar plates. The median and interquartile ranges were calculated and compared for analysis. For survival time analysis, mice were euthanized according to humane endpoints that were approved by IACUC (inability to ambulate after tactile stimulation). Differences in survival were compared by the Log Rank test.

3.1.2 Results

Mice (n=8/group) were infected with $1.3 \times 10^8$ CFU and treated for 3 days with RBT or RIF at 5 mg/kg. RBT significantly improved survival compared to both PBS control and RFP and RFP did not improve survival vs. control (FIG. 2; RBT: survival of about 80%, RFP and PBS/control: survival of <20% 2 days post infection).

Figure 3:
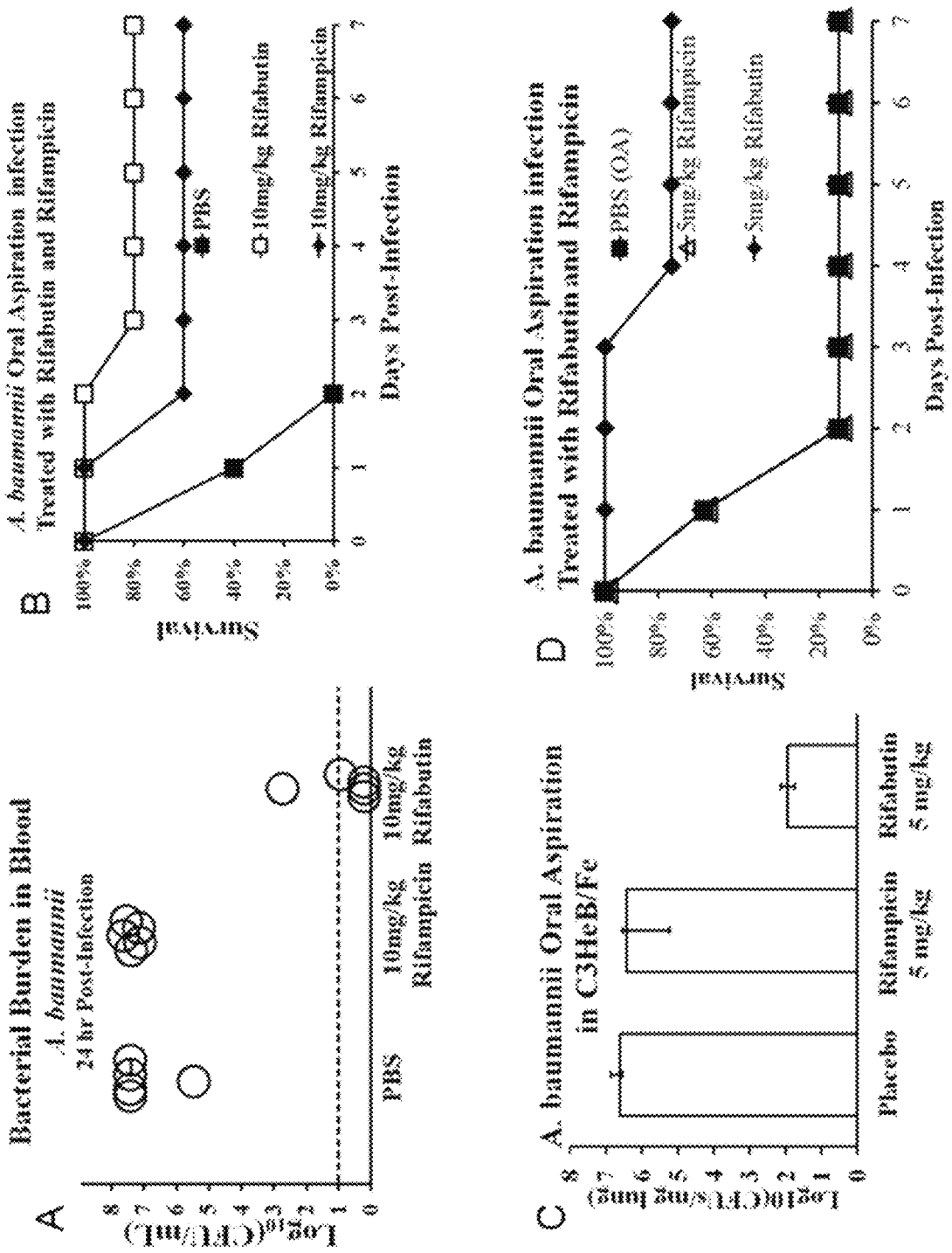
FIG. 3. RBT vs RIF therapy in an *A. baumannii* lung infection mouse model. C3H mice (n=5) were infected with *A. baumannii* HUMC1 (antibiotic-resistant strain) and mice were treated with 10 mg/kg/daily for 3 days with RIF or RBT by oral gavage. A) At 24 hrs, blood was collected and there was a significant reduction in CFUs in the RBT treated group and B) a modest survival benefit. C) The experiment was repeated with a largest group of mice (n=8) and the dose was decreased to 5 mg/kg/daily for 3 days with RIF or RBT by oral gavage. At 24 hrs, mice were sacrificed and lungs were harvested and homegates were plated to determine the bacterial density in the lung. Mice that received the rifabutin treatment had significantly lower CFUs in the lung at 24 hrs post infection and D) survival was also significantly improved.

For a separate cohort of mice (n=8 mice per group), lungs were collected at 24 hrs post infection and the bacterial burden was determined by quantitative culture. RBT reduced CFUs compared to both PBS and RFP, and RFP treatment did not reduce CFUs compared to control (FIG. 3).

3.2 In-Vivo Bacteremia Model

Mice (n=8 per group) were infected with $2 \times 10^7$ treated for 3 days with RBT or RIF at 10 mg/kg. RBT significantly improved survival compared to both RFP and PBS control (FIG. 4; RBT: survival of about 100%, RFP: survival of about 50%, both compared to PBS/control with 0% 2 days post infection).

In a separate cohort of mice (n=8 per group), blood was collected at 24 hrs post infection and the bacterial burden was quantified.

RBT significantly reduced CFUs compared to both PBS control and RFP (FIG. 5).

Example 11

A. baumannii Strain Panel with Rifabutin/Rifampin MICs

TABLE 11

Rifampin and Rifabutin MIC media comparison

|  | RPMI | CAMHB |
|---|---|---|
| Rifampin | | |
| $MIC_{90}$ (µg/mL) | 25 | 6.25 |
| $MIC_{50}$ (µg/mL) | 12.5 | 3.13 |
| Rifabutin | | |
| $MIC_{90}$ (µg/mL) | 3.13 | 6.25 |
| $MIC_{50}$ (µg/mL) | 0.39 | 3.13 |

Example 12

High Throughput Compound Screening-ReFRAME Library

Figure 7:
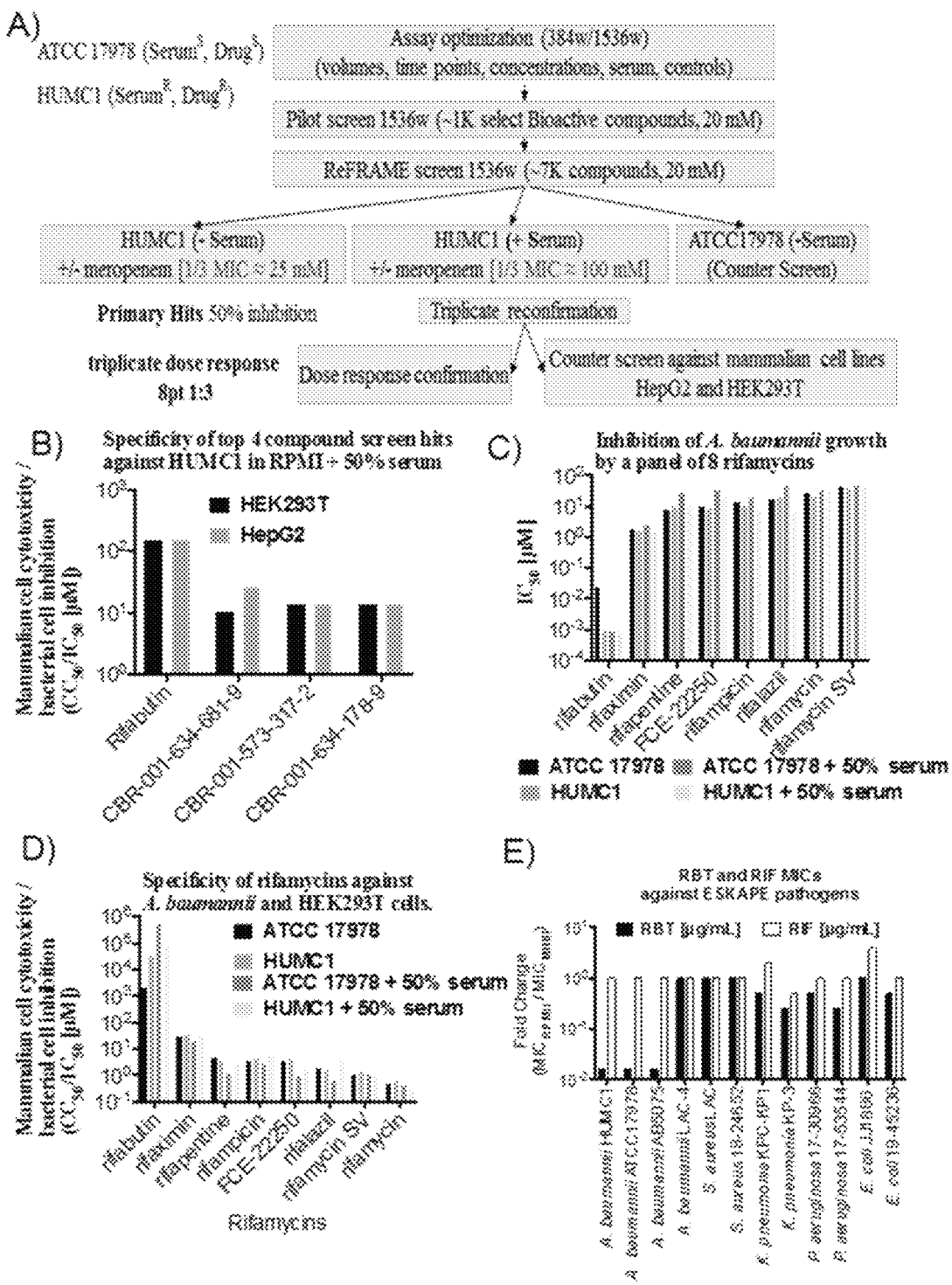
FIG. 7. Summary of the compound screening assay used for the identification of rifabutin. A) The ReFRAME compound library, a curated chemical library that is comprised of structurally and functionally diverse chemicals, including FDA approved drugs. 11,862 chemicals were screened in total and rifabutin was identified as the most active hit. *A. baumannii* ATCC 17978 and HUMC1 were selected as representative antibiotic-sensitive and extensively drug-resistant strains. B) Specificity (mammalian cell cytotoxicity/inhibition of bacteria growth; $CC_{50}/IC_{50}$) of the top 4 compound screen hits against *A. baumannii* HUMC1 and HEK293T and HepG2 mammalian cells. C) To determine if *A. baumannii* are hypersusceptible to rifamycins in general, the $IC_{50}$ was determined against ATCC 17978 and HUMC1 for 8 rifamycins. D) Specificity (mammalian cell cytotoxicity/inhibition of bacteria growth; $CC_{50}/IC_{50}$) of 8 rifamycins were tested against *A. baumannii* ATCC17978, HUMC1, and HEK293T mamillian cells, in RPMI with and without 50% serum. E) MICs were determined for RBT and RIF against a panel of ESKAPE clinical isolates.

The ReFRAME library is a curated small molecule library that represents over 10,000 compounds that cover small molecules with previously characterized activity, including antimicrobial activity. The Inventors' primary goal was to identify novel compounds that were active against the Inventors' well characterized XDR, hyper-virulent clinical isolate of A. baumannii HUMC1 (FIG. 7A). However, the Inventors didn't want to miss potential hits that would be active against a less antibiotic-resistant target and therefore included a counter screen against the antibiotic susceptible ATCC 17978 strain. The Inventors selected RPMI to be used as the culture medium as it is less nutrient rich as compared to MHII. It has been previously reported that serum exposure induces gene expression changes in the bacteria and therefore serum was included to help simulate the bloodstream environment. The Inventors were concerned that any chemicals with high protein binding affinity would be missed during the screen so the Inventors also included an RPMI group without the addition of serum to model less stringent conditions. Lastly, the library was screened against mammalian cells to evaluate toxicity.

In total the Inventors screened 11,862 chemicals at 20 µM as an initial screen. The screen resulted in a hit rate of 0.52%; 62 putative hits were identified for follow up confirmation in a serial dose response screen. About half of the compounds ($^{32}/_{62}$) were validated to inhibit 50% of bacterial growth ($IC_{50}$) at a concentration of less than 20 µM. These compounds were also assessed for cytotoxicity and 4 compounds had a favorable specific activity ($IC_{50}$<20 µM) and low toxicity ($CC_{50}/IC_{50}$>10); of these rifabutin was the most potent (i.e., had the lowest MICs, FIG. 7B).

Example 13

Rifabutin Vs Other Rifamycins

It was unexpected that RIF and RBT would have significantly different $IC_{50}$ values and the Inventors therefore tested a panel of 8 rifamycins to confirm activity using a more sensitive 11-point dose response curve. The Inventors evaluated the $IC_{50}$ against antibiotic-resistant and -susceptible A. baumannii strains in RPMI with and without serum (FIG. 7C). Toxicity was also determined against 2 eukaryotic cell lines. RBT was confirmed to be the most potent and the most specific rifamycin tested (FIG. 7D).

Example 14

Confirmation of Rifabutin Activity by MIC

The MIC of each antibiotic was determined using the broth microdilution method against A. baumannii HUMC1 and the Inventors were able to confirm the previously observed differences in activity from the chemical screen. In RPMI, the MIC of RBT (0.0156 µg/mL) was 200-fold lower as compared to RIF (3.125 µg/mL) (FIG. 7E). However, there was no difference in MIC when the bacteria were cultured in MHII (MIC=3.125 µg/mL for both RBT and RIF) (FIG. 7E).

The Inventors also tested a panel of antibiotic susceptible or resistant isolates of Staphylococcus aureus, Klebsiella pneumoniae, Pseudomonas aeruginosa, and E. coli clinical isolates to determine if the decreased MIC observed in RPMI was generalizable to other bacteria. The Inventors did not find a universal improvement against other species tested (FIG. 7E).

Example 15

MHII Vs RPMI Effects on RBT MIC

MHII Antagonizes RBT Activity

The Inventors mixed RPMI and MHII media in equal parts together and used this media to test the MIC. If the MHII media contained a component that antagonized RBT potency, the Inventors would expect that the MIC of RBT in hybrid RPMI-MHII media to be similar to the MIC of bacteria cultured in 100% MHII. In contrast, if the RPMI contained a component that promoted the activity RBT, then the Inventors would expect a MIC in the hybrid media to be closer to the MIC when the bacteria are cultured in 100% RPMI. The MICs of RBT was 4 and 8 µg/mL in the 100% MHII and hybrid media respectively (Table 12, Fig. S1). This result suggested that the MHII media antagonized the activity of RBT.

Growth Rate

The Inventors sought to understand the drivers responsible for the change in RBT potency in RPMI versus MHII media. One possibility was that the bacteria grow more slowly when cultured in RPMI vs MHII, which could then slow down antimicrobial effect. Another way to slow bacterial grow is to alter the temperature of the cultures. However, the Inventors did not observe any difference in the RIF vs. RBT MICS when A. baumannii HUMC1 was cultured at lower temps of 25° C. compared to culture at the normal temp of 37° C. in MHII or RPMI (Table 12). Therefore, the growth rate alone was not responsible for the differences in the observed antibiotic activity.

Carbon Source and Essential Nutrients

The primary carbon source in RPMI is glucose and the primary carbon source in MHII is proteins/peptides from the beef extract and casein digest. The Inventors evaluated if differences in central carbon metabolism was responsible for observed differences in antibiotic activity by the Inventors spiking glucose into MHII at 1× and $^{1}/_{10}$×the concentration present in RPMI. No difference in MIC was observed against A. baumannii HUMC1 in MHII with the different amounts of glucose added [Table 12].

MHII Fractions and Digested Products

The Inventors collected MHII media fractions based on size using molecular weight cutoff columns. The Inventors collected the <10 kDa fraction and spiked the fraction in RPMI media and again determined the MIC against RBT and RIF. The Inventors found that the addition of this fraction was sufficient to inhibit the activity of RBT (Table 12, FIG. 2).

The Inventors therefore focused on this low molecular weight fraction. The Inventors further separated the <10 kDa fraction by extracting the aqueous and organic phases by an acetonitrile liquid-liquid extraction. The addition of the purified aqueous layer to RPMI did not increase the MIC of RBT as observed in MHII. However, addition of the organic layer to RPMI did increase the MIC of RBT (Table 12). These results suggested that the material antagonizing RBT in MHII was protein-based.

If small molecular weight proteins or peptides present in MHII were the cause of the increase in MIC, the Inventors would expect that digestion of the proteins in the extracted organic layer would decrease the MIC to an equivalent value to that seen in RPMI. However, the Inventors did not observe a decrease in the MIC of RBT by treating the <10 kDa fraction with proteinase K (Table 12). If low molecular carbohydrate components present in MHII were the cause of the increase in MIC of RBT, the Inventors would expect that oxidation of carbohydrates by sodium periodate would reverse the effect. Just as with the proteinase K treatment, the Inventors did not observe a decrease in MIC or RBT upon the addition of sodium periodate treated <10 kDa MHII fraction (Table 12).

The Inventors sought to determine the effect of free amino acids on the activity of RBT. The Inventors started by adding mixed amino acids (essential or nonessential) and found that addition of each mixture had an antagonistic effect on the activity of RBT (Table 12). The Inventors then tested individual amino acids from the nonessential group to determine the contribution of each amino acid species and the Inventors found that RBT activity was inhibited by the addition of L-histidine and L-tryptophan (Table 12).

Due to amino acid mediated antagonism of RBT activity, the Inventors hypothesized that RBT, and not RIF, was entering the cell through amino acid transporters. Therefore, if the Inventors could knock-out the relevant transporter, the Inventors would inhibit RBT entry into the cell and the Inventors would observe an increase in the MIC. Amino acid transport system are redundantly encoded in the *A. baumannii* genome and the Inventors evaluated single gene transposon-disrupted mutants of apoP, tryP, hisM, mtr, hisP, and hisJ to determine if the Inventors could observe a higher shift in MIC. No single disruptant mutant displayed and difference in MIC which would indicate that a RBT may enter the cell through more than 1 transporter (Table 13).

TABLE 12

MICs were performed against HUMC1 in RPMI
*A. baumannii* HUMC1 MIC

| | RBT [μg/mL] |
|---|---|
| Controls | |
| MHII | 4.00 |
| RPMI | 0.02 |
| Temperature | |
| 25° C., MHII | 4.00 |
| 25° C., RPMI | 0.05 |
| Glucose Supplementation | |
| MHII + 200 mg/L glucose | 2.00 |
| MHII + 2,000 mg/L glucose | 2.00 |
| Modified RPMI | |
| 5X RPMI | 0.06 |
| RPMI Supplemented with MHII | 8.00 |
| Efflux Pump Inhibitor | |
| CCCP (2 μg/mL) | 0.05 |
| thioridazine (16 μg/mL) | 12.50 |
| Fractionated MHII Spiked Into RPMI | |
| 10-30 kDa MHII Fraction | 8.00 |
| <10 kDa MHII Fraction | 8.00 |
| Acetonitrile Treated <10 kDa MHII Fraction | |
| Aqueous Layer | 0.03 |
| Organic Layer | 4.00 |
| Organic Layer, Proteinase K Digested | 4.00 |
| Organic layer, Sodium Periodate Treated | 4.00 |
| Supplemented RPMI | |
| Non-Essential Amino Acid Solution | 0.78 |
| Essential Amino Acid Solution | 1.56 |
| L-Arginine (0.5 mM) | 0.05 |
| Glutamic Acid (0.5 mM) | 0.05 |
| Glycine (0.5 mM) | 0.05 |
| Leucine (1 mM) | 0.05 |
| L-Histidine (0.5 mM) | 1.56 |
| L-Tryptophan (0.125 mM) | 1.56 |

MICs were performed against HUMC1 in RPMI, unless otherwise specified, to determine which component of MHII inhibits the activity of RBT. The MIC for CCCP and thioridazine alone are 8 and 64 μg/mL respectively.

TABLE 13

Rifabutin MICs against *A. baumannii*
AB5075 transposon disruption mutants

| | | RBT (μg/mL) | |
|---|---|---|---|
| Strain | Disrupted Gene | MHII | RPMI |
| HUMC1 | | 6.25 | 0.05 |
| AB5075-UW | | 6.25 | 0.05 |
| AB00188 | aroP | 3.13 | 0.05 |
| AB00190 | aroP | 6.25 | 0.05 |
| AB03015 | aroP | 6.25 | 0.05 |
| AB02204 | aroP | 6.25 | 0.05 |
| AB09979 | aroP | 0.78 | 0.05 |
| AB09980 | tryP | 3.13 | 0.05 |
| AB00215 | tryP | 6.25 | 0.05 |
| AB03612 | hisM | 3.13 | 0.05 |
| AB03616 | hisM | 6.25 | 0.05 |
| AB03618 | hisM | 6.25 | 0.05 |
| AB06383 | hisJ | 6.25 | 0.05 |
| AB07813 | mtr | 25 | 0.05 |
| AB02205 | aroP | 3.13 | 0.05 |
| AB07354 | aroP | 6.25 | 0.05 |
| AB07356 | aroP | 1.56 | 0.05 |
| AB09982 | tryP | 6.25 | 0.05 |
| AB00216 | tryP | 1.56 | 0.05 |
| AB06392 | hisP | 0.78 | 0.05 |
| AB06386 | hisP | 0.78 | 0.05 |
| AB06105 | aroP | 3.13 | 0.05 |
| AB03608 | hisJ | 3.13 | 0.05 |

Mutants were deficient in amino acid transport genes. MIC assay was done in both MHII and RPMI media. AB5075-UW is the parent strain for the transposon mutants.

Rifabutin MICs against *A. baumannii* AB5075 transposon disruption mutants. Mutants were deficient in amino acid transport genes. MIC assay was done in both MHII and RPMI media. AB5075-UW is the parent strain for the transposon mutants.

TABLE 14

Rifabutin MICs against *A. baumannii* AB5075 transposon disruption mutants

| Strain | AB locus | Disrupted gene | MHII | RPMI |
|---|---|---|---|---|
| AB05672 | ABUW_2165 | | 6.25 | 3.13 |
| AB05673 | ABUW_2165 | | 3.13 | 3.13 |
| AB05674 | ABUW_2165 | | 3.13 | 1.56 |
| AB10057 | ABUW_3811 | DID | 3.13 | 0.05 |
| AB10058 | ABUW_3811 | | 3.13 | 0.05 |
| AB06731 | ABUW_2557 | hypothetical protein(epoxyqueuosine reductase QueH) | 3.13 | 0.05 |
| AB06732 | ABUW_2557 | | 6.25 | 0.05 |
| AB06076 | ABUW_2318 | cytosine permease | 3.13 | 0.05 |
| AB06077 | ABUW_2318 | | 1.56 | 0.05 |
| AB05837 | ABUW_2228 | TonB-dependent receptor | 3.13 | 0.05 |
| AB05838 | ABUW_2228 | | 3.13 | 0.05 |
| AB05361 | ABUW_2062 | phospholipase D family protein | 1.56 | 0.05 |
| AB05362 | ABUW_2062 | | 1.56 | 0.05 |
| AB07566 | ABUW_2893 | hypothetical protein | 0.78 | 0.05 |
| AB07567 | ABUW_2893 | | 0.78 | 0.05 |
| AB02034 | ABUW_0745 | hypothetical protein | 0.78 | 0.05 |
| AB02035 | ABUW_0745 | | 1.56 | 0.05 |
| AB09112 | ABUW_3470 | Zn-dependent hydrolase | 0.78 | 0.05 |
| AB09114 | ABUW_3470 | | 0.78 | 0.05 |
| AB01188 | ABUW_0449 | hypothetical protein | 1.56 | 0.05 |
| AB01192 | ABUW_0449 | | 1.56 | 0.05 |
| AB04576 | ABUW_1741 | outer membrane protein assembly factor BamA | 1.56 | 0.05 |
| AB05479 | ABUW_2100 | LysR family transcriptional regulator | 3.13 | 0.05 |
| AB05480 | ABUW_2100 | | 1.56 | 0.05 |
| AB05756 | ABUW_2194 | acyl-CoA dehydrogenase | 1.56 | 0.05 |
| AB05757 | ABUW_2194 | | 6.25 | 0.05 |
| AB06047 | ABUW_2307 | biotin synthase | 0.05 | 0.05 |
| AB06049 | ABUW_2307 | | 0.05 | 0.05 |
| AB06089 | ABUW_2322 | integrase | 3.13 | 0.05 |
| AB06091 | ABUW_2322 | | 6.25 | 0.05 |
| AB05348 | ABUW_2057 | alcohol dehydrogenase | 1.56 | 0.05 |
| AB05089 | ABUW_1933 | NADP-dependent fatty aldehyde dehydrogenase | 1.56 | 0.05 |
| AB04593 | ABUW_1750 | HAD-superfamiy hydrolase | 3.13 | 0.05 |
| AB04594 | ABUW_1750 | | 3.13 | 0.05 |
| AB02891 | ABUW_1069 | NADH dehydrogenase | 3.13 | 0.05 |
| AB02892 | ABUW_1069 | | 6.25 | 0.05 |
| AB06694 | ABUW_2539 | IS4 family transposase | 3.13 | 0.05 |
| AB06695 | ABUW_2539 | | 3.13 | 0.05 |
| AB01494 | ABUW_0559 | putative phage-related membrane protein | 3.13 | 0.05 |
| AB01495 | ABUW_0559 | | 6.25 | 0.05 |
| AB06821 | ABUW_2586 | allophanate hydrolase | 3.13 | 0.05 |
| AB06822 | ABUW_2586 | | 3.13 | 0.05 |
| AB04749 | ABUW_1817 | putative peroxidase(alpha/beta hydrolase) | 3.13 | 0.05 |
| AB04750 | ABUW_1817 | | 3.13 | 0.05 |

MIC assay was done by culturing the bacteria in either MHII or RPMI media.

Figure 8:
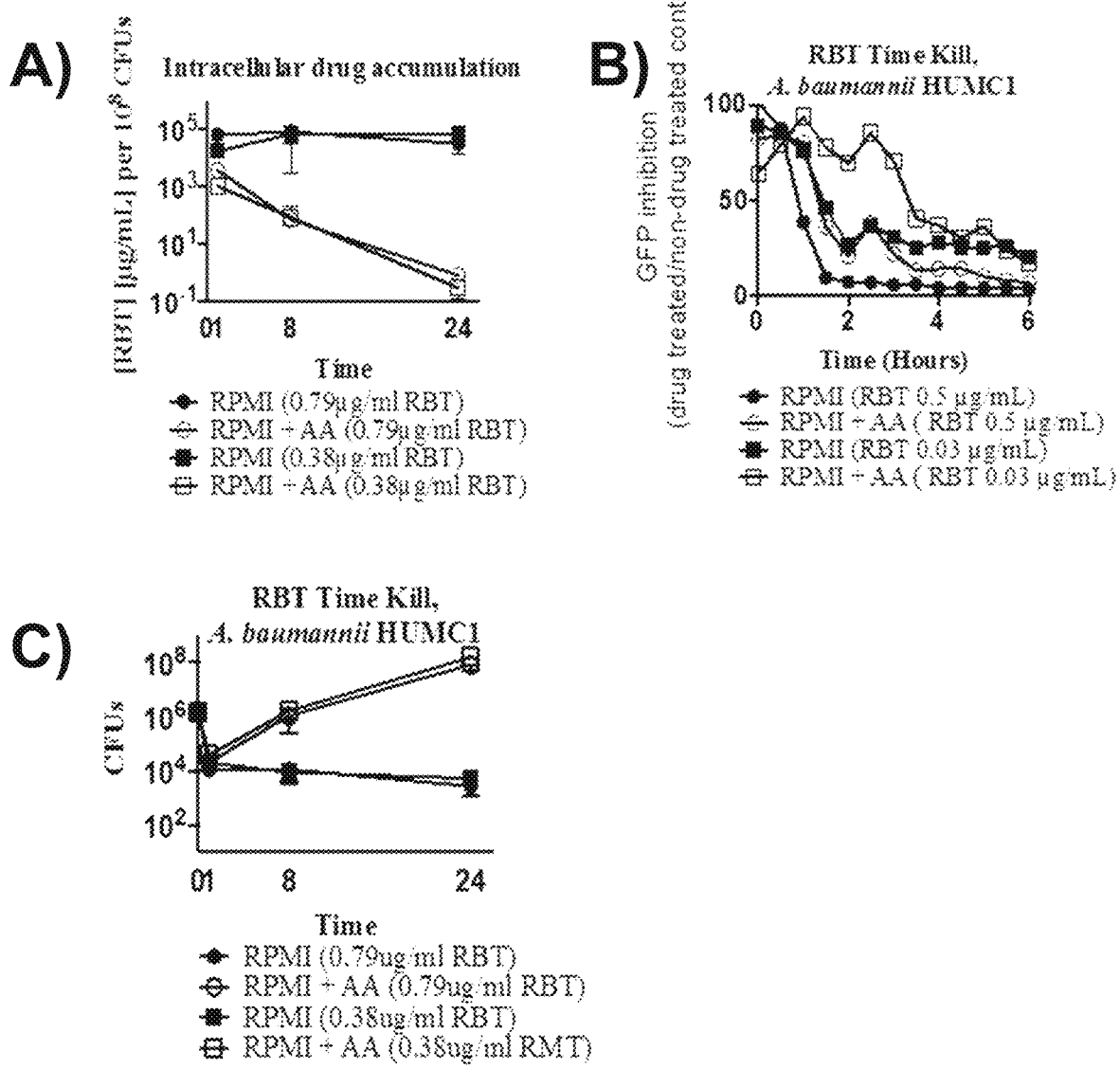
FIG. 8. Intracellular accumulation of RBT. An overnight culture of *A. baumannii* HUMC1 was subcultured in fresh RPMI, with or without supplemented amino acids (AA). A) The number of viable cells was determined by plating serial dilutions on agar plates at 0, 1, 8, and 24 hours and enumerating CFUs. B) Additionally, bacteria were harvested, washed, and lyzed to quantify the intracellular concentration of RBT by LC-MS/MS. C) A GFP expressing reporter strain of *A. baumannii* HUMC1 was cultured in RPMI, with or without supplemented amino acids, and challenged with RBT. The fluorescence intensity was measured every 30 minutes for 6 hours using a fluorescent microplate reader. The addition of amino acids (open triangles and open circles) resulted in less inhibition of GFP fluorescence which is consistent with the higher MICs observed in these same conditions.

Lastly, the Inventors sought to measure the accumulation of RBT in the cell by LC/MS/MS (FIG. 8A). Bacteria were incubated in RPMI with or without amino acid supplementation and treated with RBT. The Inventors observed a greater reduction in CFUs when bacteria were cultured in RPMI alone at the 8 and 24 hrs timepoints (FIG. 8B). CFU number was inversely correlated with intracellular drug accumulation which indicates that inhibition of RBT entry into the cell resulted in a greater number of surviving bacteria (FIG. 8A-B). To test if RBT was functioning by inhibiting transcriptions, as compared to an uncharacterized mechanism of action, the Inventors challenged a GFP expressing reporter strain with RBT in RPMI with and without amino acid supplementation. The Inventors observed that the greater inhibition of transcription was consistent with the intracellular accumulation of RBT in RPMI vs RPMI supplemented with amino acids (FIG. 8C).

Example 16

In Vivo RBT Activity

Figure 9:
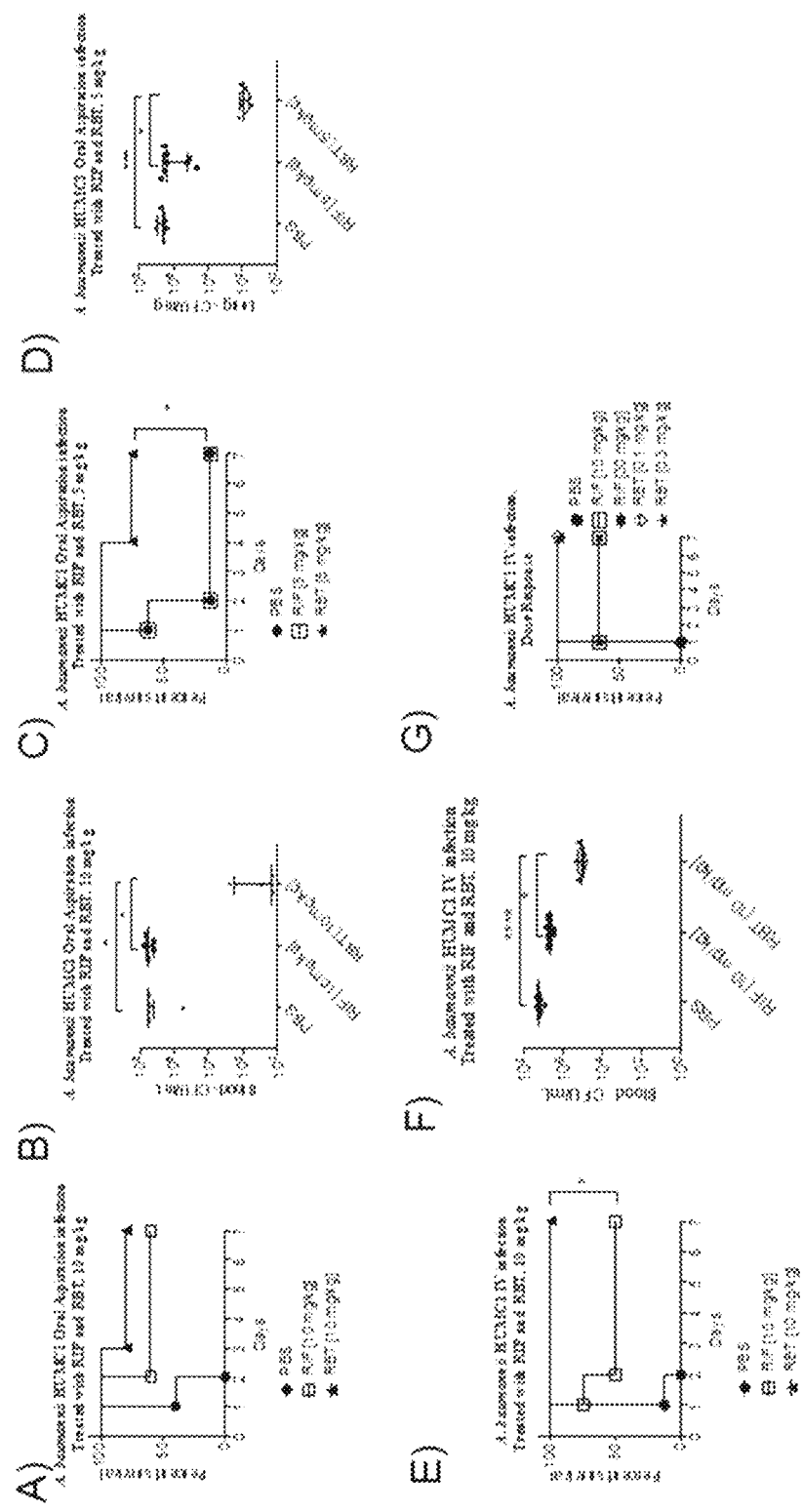
FIG. 9. Efficacy of RBT in vivo. A) C3H mice (n=5) were infected (oral aspiration pneumoniae model) with *A. baumannii* HUMC1 (carbapenem-resistant strain) and mice were treated with 10 mg/kg/daily for 3 days with RIF or RBT by oral gavage. At 24 hrs, blood was collected and there was a significant reduction in CFUs in the RBT treated group and B) a modest survival benefit. C) The experiment was repeated with a larger group of mice (n=8) and the dose was decreased to 5 mg/kg/daily for 3 days with RIF or RBT by oral gavage. At 24 hrs, mice were sacrificed and lungs were harvested, homogenized, and serial dilutions were plated on agar plates and CFUs were quantified. Mice that received the RBT treatment had significantly lower CFUs in the lung at 24 hrs post infection and D) survival was also significantly improved. E) C3H mice (n=8) were infected via tail vein injection with *A. baumannii* HUMC1. Mice were treated with 10 mg/kg/daily RIF or RBT for 3 days by oral gavage. Mice that received the RBT treatment had improved survival and F) significantly lower CFUs in the blood at 1 hrs. G) C3H mice were infected IV and treated with RIF or RBT.

The Inventors next evaluated if the potent activity of RBT would translate to enhanced efficacy vs. RIF in in vivo mouse models of disease. The Inventors first tested the efficacy of the RBT vs. RIF in an *A. baumannii* pneumonia model. Mice were infected with *A. buamnannii* HUMC1 and treated with treated with 10/mg/kg/day RIF or RBT for 3 days. At 24 hours, RBT-treated mice had a 7-log reduction in the median CFUs in the blood as compared to RIF-treated mice. There was a modest improvement in survival as well. (FIG. 9A-B).

The Inventors repeated the experiment with a reduced dose of each drug to determine if the efficacy difference would be enhanced (presuming greater potency of RFB vs. RIF). Mice were infected and treated with 5 mg/kg/daily of either drug or placebo for 3 days, and lungs were harvested and the bacterial density of the organs was quantified. RBT-treated mice had significantly reduced lung CFUs and significantly improved survival (FIG. 9C-D). Mice that were treated with 5 mg/kg of RIF did not do any better as compared to the PBS control group. This experiment validated the initial mouse experiment and the Inventors' hypothesis that RBT is more potent in vivo as compared to RIF.

Next, the Inventors tested if RBT was more effective than RIF in an intravenous model of infection. Mice were infected IV with HUMC1 and treated with 10/mg/kg/day RIF or RBT for 3 days. At 1 hour, RBT-treated mice had significantly lower CFUs in the blood as compared to RIF-treated mice. Additionally there was also a significant improvement in survival as well. (FIG. 9E-F). The Inventors tested the minimum dose required for RBT or RIF would allow for protection in an IV infection model. The Inventors found that RBT was fully protective when dosed at 100× lower concentration as compared to RIF which was only partially protective (FIG. 9G).

Additionally, the Inventors observed that RBT was more effective as compared to RIF in a murine neuropenic lung infection model. Lastly, multiple doses of RBT and RIF were tested in a *G. mellonella* infection model. Consistent with dose titration studies that were one in mice, the Inventors also observed that RBT was protective at significantly lower doses as compared to RIF.

Figure 10:
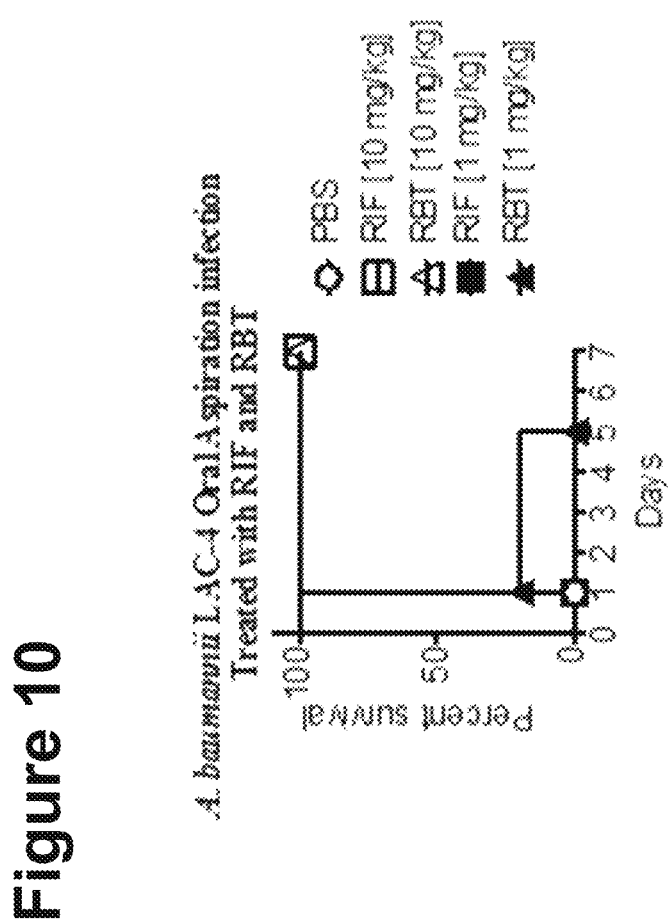
FIG. 10. RPMI MIC predicts in vivo response to treatment. C3H mice were infected with *A. baumannii* LAC-4, a strain that has the same MIC for RIF and RBT in RPMI, and mice were treated with 10 mg/kg/daily or 1 mg/kg for 3 days with RIF or RBT. Consistent with the RPMI MIC data, no difference was observed in vivo.

The Inventors identified that the LAC-4 strain was not hypersensitive to RBT and was equally sensitive to RBT and RIF in the RPMI MIC assay. The Inventors then tested if this equal susceptibility phenotype would be reproduced in vivo. Consistent with the in vitro RPMI MIC data, there was no difference in efficacy of RBT or RIF against LAC-4 (FIG. 10). There was also no difference in efficacy of RBT vs RIF against LAC-4 in a *G. mellonella* infection model.

Example 17

Discussion

*A. baumannii* is one of the few bacteria strains of which have developed resistance to all available antibiotics. National surveillance data confirm that an astonishing 50% of *A. baumannii* isolates from US intensive care units are XDR, far higher than for other pathogens, including *Pseudomonas aeruginosa* (20%) or *Klebsiella* spp. (10%). Approximately 23,000 and 75,000 cases of XDR *A. baumannii* infections occur annually in the US and globally (in developed countries), respectively.

High throughput chemical screening assays have been a standard practice for the pharmaceutical industry for decades. However, these libraries have been screened many times, and rarely do new screens of the same library identify novel compounds that have not been previously identified. One fundamental limitation is that the culture conditions will influence the physiologic state of the bacteria. A change in cellular physiology could alter the availability of the drug target or affect drug metabolism. This may result in a culture-dependent susceptible phenotype that selects for false positives or a resistant phenotype that selects for false negatives. Changes in the carbon source during culture can result in significant overall changes in both gene expression and protein translation. These metabolic changes have been shown to have direct effects on antibiotic activity. A significant amount of time, labor, and financial resources may have been lost to the characterization of drug candidates that target a metabolic process that is active in vitro but not in vivo.

The modification of in vitro culture conditions to best reflect in vivo conditions are needed for the best chance of success. For example, some pathogens, such as *Mycobacterium tuberculosis* (M. tb), are likely to reside in host macrophages which constitute a significantly different environment as compared to nutrient rich broth culture of the bacteria alone. Modified screening protocols that involved screening chemicals against M. tb infected macrophages resulted in the identification of novel compounds. To identify rifabutin, the Inventors modified the culture conditions to better reflect the in vivo environment of a bloodstream infection by culturing the bacteria in a relatively nutrient depleted media with the addition of serum. The Inventors found that RFB was much more potent than RIF when tested in the depleted media plus serum but not in rich media. Validating the relevance of this approach is that RBT was also more effective in vivo when treating mice infected intravenously or with pneumonia caused by an XDR hypervirulent clinical isolate of *A. baumannii*. This finding would not have been made had the initial screen been conducted with rich media.

The relative superiority of RFB over RIF is highly significant due to a recent, randomized, controlled clinical trial that found a non-significant trend to improved clinical cure, with a significant improvement in microbiological eradication when adding rifampin to colistin for treatment of XDR *A. baumannii* infections.https://paperpile.com/c/XyTdki/xEeXU Given that RIF had some effect clinically, and that RFB appears far more potent and effective in pre-clinical models, the Inventors believe that the addition of adjunct RFB, as compared to RIF, could serve as a critically needed new therapeutic option for patients with infections caused by XDR *A. baumannii*, potentially resulting in superior survival compared to the current standard of care. As RBT is already commercially available, these results can be immediately translated.

The invention claimed is:

1. A method of treating a mammalian subject infected with *Acinetobacter*, comprising:
   administering a therapeutically effective amount of rifabutin to the mammalian subject,
   wherein the rifabutin is co-administered with colistin but not with another therapeutically active agent, and
   wherein the administered amount of the rifabutin with the colistin is effective for improving survival of the mammalian subject compared to a mammalian subject infected with the *Acinetobacter* who is not administered with a therapeutically active agent or who is administered with the rifampin as a sole therapeutically active agent.

2. The method of claim 1, wherein the *Acinetobacter* is *Acinetobacter baumannii*.

3. The method of claim 1, wherein the mammalian subject is a human patient.

4. The method of claim 3, wherein the method comprises a time lag of at least about 4 h between administration of the rifabutin and administration of the colistin.

5. The method of claim 4, wherein the Acinetobacter infection is caused by multi-drug resistant Acinetobacter bacteria.

6. The method of claim 5, wherein the Acinetobacter infection is an infection in respiratory tract, blood, circulation system, urinary tract, skin, surgical-site, or a combination thereof, of the human patient, or wherein meningitis is identified in the human patient.

7. The method of claim 6, wherein the *Acinetobacter* infection is a nosocomial *Acinetobacter* infection.

8. The method of claim 7, wherein the rifabutin is administered in a dose of 60 mg to 600 mg per day.

9. A method of treating an *Acinetobacter* infection in a human subject, comprising:
   administering rifabutin to the human subject in need thereof, wherein the rifabutin is administered in a daily dose of 60 mg to 600 mg with colistin but not with another therapeutically active agent, and
   wherein the administered dose of the rifabutin with the colistin is effective for improving survival of the human subject compared to a human subject infected with the *Acinetobacter* who is not administered with a therapeutically active agent or who is administered with the rifampin as a sole therapeutically active agent.

10. The method of claim 9, wherein the *Acinetobacter* infection is an infection caused by bacteria selected from the group consisting of *Acinetobacter baumannii*, *Acinetobacter lwoffii*, *Acinetobacter calcoaceticus*, *Acinetobacter nosocomialis*, and *Acinetobacter pittii*.

11. The method of claim 9, wherein the *Acinetobacter* infection is caused by multi-drug resistant *Acinetobacter* bacteria.

12. The method of claim 9, wherein the *Acinetobacter* infection is an *Acinetobacter* infection of the respiratory tract, blood, circulation system, urinary tract, skin, surgical-site, catheter-site, or a combination thereof, of the human subject, or wherein meningitis is identified in the human subject.

13. The method of claim 9, wherein the *Acinetobacter* infection is a nosocomial *Acinetobacter* infection.

14. A method of treating a mammalian subject infected with *Acinetobacter*, comprising:

administering to the mammalian subject a therapeutically effective amount of rifabutin and colistin but not with another therapeutically active agent.

15. The method of claim 14, wherein the *Acinetobacter* is *Acinetobacter baumannii*.

16. The method of claim 14, wherein the mammalian subject is a human patient.

17. The method of claim 14, wherein the method comprises a time lag of at least about 4 h between administration of the rifabutin and administration of the colistin.

18. The method of claim 14, wherein the rifabutin is administered in a dose of 60 mg to 600 mg per day.

* * * * *